(12) United States Patent
Åkerström et al.

(10) Patent No.: US 10,350,268 B2
(45) Date of Patent: Jul. 16, 2019

(54) MEDICAL USE OF THE RADICAL SCAVENGER AND ANTIOXIDANT ALPHA-1-MICROGLOBULIN

(75) Inventors: Bo Åkerström, Lund (SE); Stefan Hansson, Lomma (SE); Martin Lennarth Olsson, Bjarred (SE); Magnus Gram, Oxie (SE)

(73) Assignee: A1M PHARMA AB, Lund (SE)

( * ) Notice: Subject to any disclaimer, the term of this patent is extended or adjusted under 35 U.S.C. 154(b) by 1521 days.

(21) Appl. No.: 13/054,188

(22) PCT Filed: Jul. 17, 2009

(86) PCT No.: PCT/EP2009/005217
§ 371 (c)(1),
(2), (4) Date: Apr. 6, 2011

(87) PCT Pub. No.: WO2010/006809
PCT Pub. Date: Jan. 21, 2010

(65) Prior Publication Data
US 2011/0190208 A1    Aug. 4, 2011

Related U.S. Application Data

(60) Provisional application No. 61/135,338, filed on Jul. 18, 2008, provisional application No. 61/189,381, filed on Aug. 18, 2008, provisional application No. 61/197,506, filed on Oct. 27, 2008.

(30) Foreign Application Priority Data

| Jul. 18, 2008 | (DK) | ................................. | 2008 01024 |
| Aug. 18, 2008 | (DK) | ................................. | 2008 01116 |
| Oct. 27, 2008 | (DK) | ................................. | 2008 01478 |

(51) Int. Cl.
*A61K 38/17* (2006.01)

(52) U.S. Cl.
CPC ................................ *A61K 38/1774* (2013.01)

(58) Field of Classification Search
None
See application file for complete search history.

(56) References Cited

U.S. PATENT DOCUMENTS

| 5,166,133 | A | 11/1992 | Houston et al. | |
| 5,910,482 | A | 6/1999 | Yallampalli et al. | |
| 6,103,691 | A | 8/2000 | Tschesche et al. | |
| 2006/0105419 | A1 | 5/2006 | Blankenberg et al. | |
| 2007/0060512 | A1* | 3/2007 | Sadeghi et al. | 514/12 |
| 2008/0133141 | A1 | 6/2008 | Frost | |

FOREIGN PATENT DOCUMENTS

| JP | 2001-348342 A | 12/2001 |
| JP | 2007-001922 A | 1/2007 |
| WO | WO 02/096414 A1 | 12/2002 |
| WO | WO 2004/017948 A2 | 3/2004 |
| WO | WO 2005/011728 A2 | 2/2005 |
| WO | WO 2005/058305 A1 | 6/2005 |
| WO | WO 2007/015841 | 2/2007 |
| WO | WO 2008/098734 A1 | 8/2008 |

OTHER PUBLICATIONS

Cola, Fast facts 30 (Complications of Blood Transfusion: Discussion and Investigation, document created May 17, 2006).*
K. Terpe ("Overview of tag protein fusions: from molecular and biochemical fundamentals to commercial systems", Appl. Microbiol Biotechnol (2003) vol. 60; 523-533).*
Oxidative stress resources (http://www.oxidativestressresource.org/, accessed Apr. 1, 2014).*
Merck Manual, http://www.merckmanuals.com/home/hormonal_and_metabolic_disorders/diabetes_mellitus_dm/diabetes_mellitus.html?qt=Type I diabetes&alt=sh#v772820 accessed May 2, 2014).*
Merck Manual (http://www.merckmanuals.com/home/brain_spinal_cord_and_nerve_disorders/movement_disorders/huntington_disease.html?qt=huntington&alt=sh) (Merck Manual, Aug. 2007).*
Allhourn et al. J. Invest Dermatol 121:640, 2003.*
MGI: Mouse facts (accessed May 31, 2015).*
Halliwell et al., "Oxidative Stress: adaptation, damage, repair and death," Free Radicals in Biology and Medicine, Third Edition, pp. 246-350, 1996.
International Search Report dated Mar. 17, 2010 in application No. PCT/EP2009/005217.
Åkerström et al., "The Lipocalin $\alpha_1$-Microglobulin Has Radical Scavenging Activity," The Journal of Biological Chemistry, vol. 282, No. 43, pp. 31493-31503, Oct. 26, 2007.
Allhorn et al., "Redox properties of the lipocalin $\alpha_1$-microglobulin: Reduction of cytochrome c, hemoglobin, and free iron," Free Radical Biology & Medicine, vol. 38, pp. 557-567, 2005.
Allhorn et al., "Heme-Scavenging Role of $\alpha_1$-Microglobulin in Chronic Ulcers," The Journal of Investigative Dermatology, vol. 121, No. 3, pp. 640-646, Sep. 2003.
Allhorn et al., "Processing of the lipocalin $\alpha_1$-microglobulin by hemoglobin induces heme-binding and heme-degradation properties," Blood, vol. 99, No. 6, pp. 1894-1901, Mar. 15, 2002.
Ascenzi et al., "Hemoglobin and Heme Scavenging," IUBMB Life, vol. 57, pp. 749-759, 2005.
Larsson et al., "The lipocalin $\alpha_1$-microglobulin binds heme in different species," Archives of Biochemistry and Biophysics, vol. 432, pp. 196-204, 2004.

(Continued)

*Primary Examiner* — James H Alstrum-Acevedo
*Assistant Examiner* — Tara L Martinez
(74) *Attorney, Agent, or Firm* — Foley & Lardner LLP

(57) ABSTRACT

Medical use of alpha-1-microglobulin (A1M) in the treatment or prophylaxis of diseases wherein oxidative stress is a responsible factor in the progress of the disease. Notably, the present invention relates to the medical use of alpha-1-microglobulin in the treatment or prophylaxis of diseases or conditions associated with the presences of free radicals and/or free haemoglobin in the subject.

28 Claims, 23 Drawing Sheets

Specification includes a Sequence Listing.

(56) References Cited

OTHER PUBLICATIONS

Nordberg et al., "Quantitative and qualitative evaluation of plasma and urine $\alpha_1$-microglobulin in healthy donors and patients with different haemolytic disorders and ahemochromatosis," Clinica Chimica Acta, vol. 386, pp. 31-37, 2007.

Olsson et al., "Up-regulation of a $\alpha_1$-microglobulin by hemoglobin and reactive oxygen species in hepatoma and blood cell lines," Free Radical Biology & Medicine, vol. 42, pp. 842-851, 2007.

Olsson et al., "The lipocalin $\alpha_1$-microglobulin protects erythroid K562 cells against oxidative damage induced by heme and reactive oxygen species," Free Radical Research, vol. 42, No. 8, pp. 725-736, Aug. 2008.

Renó et al., "Surface-adsorbed $\alpha_1$-microglobulin modulation of human fibroblasts spreading and matrix metalloproteinases," Biomaterials, vol. 25, pp. 3439-3443, 2004.

Dröge, "Free Radicals in the Physiological Control of Cell Function," Physiol. Rev., vol. 82, pp. 47-95, 2002.

Kaumeyer et al., "The mRNA for a proteinase inhibitor related to the HI-30 domain of inter-$\alpha$-trypsin inhibitor also encodes $\alpha$-1-microglobulin (protein HC)," Nucleic Acids Research, vol. 14, No. 20, pp. 7839-7850, 1986.

Halliwell et al., "The Definition and Measurement of Antioxidants in Biological Systems," Free Radical Biology & Medicine, vol. 18, No. 1, pp. 125-126, 1995.

Segal, "How Neutrophils Kill Microbes," vol. 23, pp. 197-223, 2005.

Sala et al., "Human $\alpha$-1-Microglobulin Is Covalently Bound to Kynureine-derived Chromophores," The Journal of Biological Chemistry, vol. 279, No. 49, pp. 51033-51041, 2004.

Traboni et al., "Sequence of a full length cDNA coding for human protein HC ($\alpha_1$microglobulin)," Nucleic Acids Research, vol. 14, No. 15, p. 6340, 1986.

Allhorn et al., "Redox properties of the lipocalin alpha-1-microglobulin: reduction of cytochrome c, hemoglobin and free iron," Lund University, pp. 1-41, Lund, Sweden, 2005.

Kwasek et al., "Production of recombinant human alpha-1-microglobulin and mutant forms involved in chromophore formation," Protein Expression and Purification, vol. 53, pp. 145-152, 2007.

Tardivel et al., "Alpha-1-microglobulin: inhibitory effect on calcium oxalate crystallization in vitro and decreased urinary concentration in calcium oxalate stone formers," Urological Research, vol. 27, pp. 243-249, 1999.

Mendez et al., "Human protein HC and its IgA complex are inhibitors of neutrophil chemotaxis," Proceedings of the National Academy of Sciences, U.S. A., vol. 83, pp. 1472-1475, 1986.

Olsson, "Alpha-1-microglobulin: Innate defence against pathological oxidation," Lund University/Dissertation, 2009, retrieved from the Internet: http://www.lu.se/lup/publication/1464287.

European Search Report dated Aug. 16, 2013 in application No. EP13172049.

Santin et al., "Collagen-Bound $_{\alpha 1}$-Microglobulin in Normal and Healed Tissues and its Effect on Immunocompetent Cells," Scand. J. Immunol. (1999) vol. 50, pp. 289-295.

Osipov, "Biological Activity of Hemoprotein Nitrosyl Complexes," Biochemistry (Moscow), vol. 72, No. 13, pp. 1491-1504, 2007.

Eurasian Search report dated Sep. 11, 2015 in application No. ER201500335.

* cited by examiner

A and B

B and C

SEQUENCE LISTING

```
<110>  Åkerstrm, Bo
       Hansson, Stefan

<120>  Medical use of the radical scavenger and anti-oxidant alpha
       1-microglobulin

<130>  P13535 PC

<160>  5

<170>  PatentIn version 3.5

<210>  1
<211>  183
<212>  PRT
<213>  Homo sapiens

<400>  1
```

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro

Glu Pro Ile Leu Ile Pro Arg
            180

<210>  2
<211>  201
<212>  PRT
<213>  Homo sapiens

<400>  2

Met His His His His His His Gly Gly Gly Gly Ile Glu
1               5                   10                  15

Gly Arg Gly Pro Val Pro Thr Pro Pro Asp Asn Ile Gln Val Gln Glu
                20                  25                  30

Asn Phe Asn Ile Ser Arg Ile Tyr Gly Lys Trp Tyr Asn Leu Ala Ile
            35                  40                  45

Gly Ser Thr Cys Pro Trp Leu Lys Lys Ile Met Asp Arg Met Thr Val
        50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
            195                 200
```

Fig. 19 (Continued)

```
<210>  3
<211>  549
<212>  DNA
<213>  Homo sapiens

<400>  3
ggccctgtgc caacgccgcc cgacaacatc caagtgcagg aaaacttcaa tatctctcgg      60
atctatggga agtggtacaa cctggccatc ggttccacct gccctggct gaagaagatc      120
atggacagga tgacagtgag cacgctggtg ctgggagagg gcgctacaga ggcggagatc     180
agcatgacca gcactcgttg gcggaaaggt gtctgtgagg agacgtctgg agcttatgag     240
aaaacagata ctgatgggag gtttctctat cacaaatcca aatggaacat aaccatggag     300
tcctatgtgg tccacaccac ctatgatgag tatgccattt ttctgaccaa gaaattcagc     360
cgccatcatg gacccaccat tactgccaag ctctacgggc gggcgccgca gctgagggaa     420
actctcctgc aggacttcag agtggttgcc cagggtgtgg gcatccctga ggactccatc     480
ttcaccatgg ctgaccgagg tgaatgtgtc cctggggagc aggaaccaga gcccatctta     540
atcccgaga                                                              549

<210>  4
<211>  603
<212>  DNA
<213>  Homo sapiens

<400>  4
atgcatcacc atcaccatca ccatcacggt ggaggagggg gtatcgaggg ccgcggccct      60
gtgccaacgc cgcccgacaa catccaagtg caggaaaaact tcaatatctc tcggatctat    120
gggaagtggt acaacctggc catcggttcc acctgcccct ggctgaagaa gatcatggac    180
aggatgacag tgagcacgct ggtgctggga gagggcgcta caggcgga tcagcatg        240
accagcactc gttggcggaa aggtgtctgt gaggagacgt ctggagctta tgagaaaaca    300
gatactgatg ggaggtttct ctatcacaaa tccaaatgga acataaccat ggagtcctat    360
gtggtccaca ccacctatga tgagtatgcc attttttctga ccaagaaatt cagccgccat    420
catggaccca ccattactgc caagctctac gggcgggcgc gcagctgag ggaaactctc     480
ctgcaggact tcagagtggt tgcccagggt gtgggcatcc ctgaggactc catcttcacc    540
atggctgacc gaggtgaatg tgtccctggg gagcaggaac cagagcccat cttaatcccg    600
aga                                                                    603

<210>  5
<211>  19
<212>  RNA
<213>  Artificial Sequence

<220>
<223>  for silencing expression of alpha-1-microglobulin

<400>  5
ccuauguggu ccacaccaa                                                    19
```

# MEDICAL USE OF THE RADICAL SCAVENGER AND ANTIOXIDANT ALPHA-1-MICROGLOBULIN

FIELD OF THE INVENTION

The present invention relates to medical use of alpha-1-microglobulin (A1M) in the treatment or prophylaxis of diseases wherein oxidative stress is a responsible factor in the progress of the disease. Notably, the present invention relates to the medical use of alpha-1-microglobulin in the treatment or prophylaxis of diseases or conditions associated with the presences of free radicals and/or free haemoglobin in the subject. The inventors of present invention have found that alpha-1-microglobulin, which is a small protein found e.g. in humans, shows extraordinary properties as antioxidant and radical scavenger. Particularly, it is disclosed that the antioxidative properties of A1M are of particularly relevance for minimizing oxidative stress in physiologically impaired cells.

BACKGROUND OF THE INVENTION

Many diseases involve unwanted oxidation of cells and molecules in the tissues and lead to formation of extremely reactive free radicals, which in turn may lead to tissue damage. Drugs with anti-oxidant properties have been developed during the last decades, but there is still a need for developing safe drugs with a broad therapeutic potential for the treatment or prophylaxis of diseases or conditions that have an oxidative stress element.

Oxidative Stress

Oxidation is a chemical process which involves loss of electrons, i.e. a compound is oxidized when one or more electrons are removed from it. The opposite chemical process is called reduction. Oxidative stress in the human organism is defined as an increased, unwanted oxidation of cells and molecules in the tissues (reviewed in 1). It arises from an imbalance between oxidants, mediators of oxidative stress, and antioxidants, agents that can either prevent oxidation, detoxify oxidants or repair oxidized molecules (FIG. 1). The most important oxidants in humans and animals are reactive oxygen species (ROS) which include hydrogen peroxide, superoxide and the hydroxyl radical. The latter two belong to a group of compounds called free radicals. Free radicals are extremely reactive compounds due to the presence of unpaired electrons in their outer electron shells. ROS- and free radical-formation can be induced by, for example, metals and the oxygen-binding organic compound heme. Heme is an iron-containing component of haemoglobin and cytochromes, which are proteins that participate in the utilization of oxygen (see below). ROS, oxidants, and free radicals react with proteins, DNA and other molecular cell- and tissue components, which leads to unwanted modifications of the target molecules and ultimately loss of cellular functions.

Free radicals and oxidants are constantly introduced to the human body, both exogenously via the environment (food, air, smoke, etc) and endogenously as by-products of normal metabolism (FIG. 1). Endogenous free radicals and oxidants are important components of the metabolism in the animal organism. A certain amount is necessary for "house-keeping" cellular processes. For example, physiological cell-signalling is dependent on a continuous production of cellular free radicals (reviewed in 2), controlled by an intricate system of cellular antioxidants. Thus, cells need to maintain a normal, well-controlled reduction/oxidation (redox)-balance both intra- and extracellularly. Oxidative stress will result when the redox balance is upset. Free radicals and the strong oxidant hypochlorite (HOCl) are also produced in white blood cells during bacterial and fungal infections as weapons to kill the pathogens (reviewed in 3). This also leads to oxidative stress.

Haemoglobin and Other Heme-Containing Proteins

Haemoglobin is one of the most common proteins in the human body. It is found in enormous quantities in the red blood cells and its function is to carry oxygen from the lungs to all cells. The oxygen is bound to the iron-containing heme-group, which gives the haemoglobin molecule its red colour. All haemoglobin is normally kept inside the red blood cells and thus prevented from contact with other cells and extracellular components. This is important because haemoglobin is toxic due to strong oxidant properties. When the red blood cells break (haemolysis) in diseases like autoimmune haemolytic anemia, sickle cell anemia and malaria or in iatrogen situations including mismatched blood transfusion, stem cell and solid organ transplantation and major surgery, oxy-haemoglobin (haemoglobin plus oxygen) is released from the red blood cells. Oxy-haemoglobin spontaneously reacts with itself by rearranging electrons in a process called auto-oxidation, forming the free radical superoxide and methaemoglobin, an oxidized form of the protein. Methaemoglobin continues to decompose, ultimately forming free globin, heme and iron. The products are oxidative as described above. Free heme, being a hydrophobic molecule, can enter cells by diffusion over the cell membrane or dissolving the membranes. Free haemoglobin (located outside the red blood cells) is therefore an inducer of tissue damage during many diseases and other pathological conditions. In addition, free oxy-haemoglobin is indirectly a vasoconstrictor because it binds nitric oxide (NO) strongly, one of the most important dilators of small blood vessels and capillaries. NO-scavenging by free oxy-haemoglobin leads to consumption of NO and subsequent constriction of the capillaries resulting in high blood pressure.

Other heme-containing proteins include NADPH-oxidase, myeloperoxidase (MPO) and mitochondrial cytochromes. The enzymes NADPH-oxidase and myeloperoxidase are found in monocytes and neutrophil granulocytes, two subsets of white blood cells. In a process called oxidative burst, these enzymes produce superoxide radicals and hypochlorite, respectively, both of which are involved in the defense against microbial infection. The most important of the mitochondrial cytochromes are cytochrome c and NADH-dehydrogenase. These enzymes are components of the respiratory complexes I-IV which convert oxygen to water by using electrons from nutrients, stored fats, etc. In this process, large amounts of free radicals, mostly superoxide anions, are produced as intermediary metabolites by the mitochondrial enzymes.

Antioxidants

Normally, oxidant activity is balanced by the activity of antioxidants, protective factors that eliminate oxidants or prevent their oxidation reactions. During conditions of extreme oxidative stress, however, the antioxidants may be overwhelmed, leading to oxidative damage to molecules and/or cells and tissues.

Both endogenous and exogenous antioxidants are described. Twenty years ago, the prevailing view was that human homeostasis was dependent on externally added antioxidants, for instance via food intake. Today, an increasing number of human antioxidants have been discovered and shown to be produced constitutively within the body, i.e. under normal, unstressed conditions. Antioxidants operate by elimination of free radicals and oxidants. They can achieve this by three major mechanisms (see FIG. 2A and figure legends for details): 1) enzymatic addition of electrons derived from cellular aerobic metabolism or other sources to the oxidants, 2) non-enzymatic addition of electrons from the antioxidant molecule itself to the oxidant, and 3) binding (scavenging) of the radicals/oxidants to the antioxidant. Examples of the first category are the enzymes superoxide dismutase (SOD), catalase, glutathione peroxidase and heme oxygenase. Examples of the second category are thioredoxin, glutathione and alpha-lipoic acid. Vitamins C and E, unsaturated fatty acids and plant flavonoids are exogenous category 2 antioxidants that are not produced in the body but can be found in food. Some of the antioxidants of the second category, for example thioredoxin and glutathione, can be re-generated by reduction of electrons from other sources (FIG. 2A). Most antioxidants in the food are poorly re-generated after reacting with their targets. Thus, the consumed (=Oxidized) vitamins C and E, etc, present oxidative stress to the tissues unless quickly removed.

Electrons which are produced by cellular aerobic metabolism (ultimately derived from nutrients, e.g. glucose, fat, proteins via the electron-carrier NADH) provide the reducing equivalents to the antioxidants of category 1, when re-generating antioxidants of category 2 and in the scavenging process (category 3) (FIG. 2A). Therefore, most antioxidants are dependent on an intact cell metabolism and only operate intra-cellularly. In fact, most antioxidants, being intracellular, are part of the normal cellular "housekeeping" machinery.

Several antioxidants are specialized against haemoglobin-induced oxidative stress. The plasma proteins haptoglobin, hemopexin and transferrin bind free, extracellular haemoglobin, heme and iron, respectively, in the blood. The cellular protein ferritin binds and stores free, cellular iron. Heme oxygenase-1 (HO-1) is produced in most cells in response to increased concentrations of haemoglobin, heme and free radicals and eliminates heme by degradation into bilirubin, carbon monoxide and free iron.

However, none of the above-mentioned antioxidants act by all three mechanisms and, accordingly, a general therapeutic use of such an antioxidant is limited. An antioxidant having all mechanisms of action would be advantageous as it will have a much more general use and be less dependent on the cellular homeostasis for functioning.

ABBREVIATIONS

ABTS, 2,2'-azino-bis(3-ethylbenzo-thiazoline-6-sulphonic acid)diammonium salt
α1M or A1M, α1-microglobulin or alpha-1-microglobulin
t-α1M; truncated α1-microglobulin or alpha-1-glycoprotein
AGP, α1-acid glycoprotein
DTT, dithiothreitol
G3DPH, glyceraldehyd-3-phosphate dehydrogenase
Hb, haemoglobin
$H_2$DCFDA, 2',7'-dichlorodihydrofluorescein diacetate
IVF, in vitro fertilization
IVH, intra ventricular brain haemorrhage
NEM, N-ethylmaleimide
PE, preeclampsia
PI, propidium iodide
ROS, reactive oxygen species;
5-IAF, 5-iodoacetamide-fluorescein
RIA, radio immuno assay
MPO, myeloperoxidase

DEFINITIONS

In describing and claiming the disclosed subject matter, the following terminology will be used in accordance with the definitions set forth below. Unless defined otherwise, all technical and scientific terms used herein have the same meaning as commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted. Although any methods and materials similar or equivalent to those described herein can also be used in the practice or testing of the present disclosure, the preferred methods and materials are described herein.

In this specification, unless otherwise specified, "a" or "an" means "one or more".

There exist different forms of haemoglobin. Adult haemoglobin (Haemoglobin A) consists of two alpha and two beta polypeptide chains (Hbα, Hbβ), each containing a non-peptide heme group that reversibly binds a single oxygen molecule. Haemoglobin A2, another adult haemoglobin component is composed of two alpha-chains and two delta chains (Hbα, Hbδ). Fetal haemoglobin (Haemoglobin F) on the other hand is the major component of haemoglobin in the fetus. This haemoglobin has two alpha- and two gamma polypeptide chains (Hbα, Hbγ).

The term "free haemoglobin", in this specification refers to free haemoglobin generally and includes total free haemoglobin, free haemoglobin A, free haemoglobin A2, free haemoglobin F, any free haemoglobin subunit (e.g. an Hbα, Hbβ, Hbδ or Hbγ chain), or any combination thereof. It further includes these haemoglobin entities in either a polypeptide (protein) or nucleotide (RNA) form, except when applied as a target for treatment. The term "free fetal haemoglobin" refers to free haemoglobin F or any subunit of haemoglobin F and includes the haemoglobin F entities in a polypeptide (protein) or nucleotide (RNA) form, except when applied as a target for treatment.

In this specification, the term "free" as used, inter alia, in the expressions "free haemoglobin" or "free haemoglobin subunits (e.g. Hbα, Hbβ, Hbδ or Hbγ chains)" refer to haemoglobin or haemoglobin subunits freely circulating in a biological fluid, as opposed to cellular haemoglobin which refers to the molecules residing inside cells. The term "free" in this sense is thus mainly used to distinguish free haemoglobin from haemoglobin which is present in intact erythrocytes.

The terms "treatment or prophylaxis" in their various grammatical forms in relation to the present invention refer to preventing, curing, reversing, attenuating, alleviating, ameliorating, inhibiting, minimizing, suppressing, or halting (1) the deleterious effects of a disorder, (2) disorder progression, or (3) disorder causative agent.

The term "effective amount" in relation to the present invention refers to that amount which provides a therapeutic effect for a given condition and administration regimen. This is a predetermined quantity of active material calculated to produce a desired therapeutic effect in association with the required additives and diluents; i.e., a carrier, or administration vehicle. Further, it is intended to mean an amount sufficient to reduce and most preferably prevent a clinically significant deficit in the activity and response of the host.

Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive. Further, the dosage to be administered will vary depending on the active principle or principles to be used, the age, weight etc. of the patient to be treated but will generally be within the range from 0.001 to 1000 mg/kg body weight/day. Moreover, the dose depends on the administration route.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine ($Gly_1$ G), Histidine (His, H), Isoleucine (Ile, I), Leucine (Leu, L), Lysine (Lys, K), Methionine (Met, $M)_1$ Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

"Identity" as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods.

The term "substantially similar" as used herein generally refers to a function, activity, or behavior that is close enough to the natural, expected, or average, so as to be considered, for all practical purposes, interchangeable. For instance, a protein with substantially similar activity would be one that has an activity level that would not be considered to be substantially more or less active than the native protein.

The term "prodrug" refers to an agent, including nucleic acids and proteins, which is converted into a biologically active form in vivo. For instance, Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein "functional variant" refers to a variant of a protein or polypeptide (e.g., a circularly permuted protein, with or without additional sequence alterations) that can perform the same functions or activities as the original protein or polypeptide, although not necessarily at the same level (e.g., the variant may have enhanced, reduced or changed functionality, so long as it retains the basic function).

DETAILED DESCRIPTION OF THE INVENTION

In present invention, it is disclosed that A1M possesses broad antioxidant properties suitable to avoid or minimize injuries caused by oxidative stress. The current concept is that the physiological function of A1M is to continuously "vacuum-clean" tissues from free radicals and oxidants, perhaps especially heme, and deliver the products to the kidneys for degradation and/or excretion. A second physiological function is to reduce oxidants and oxidized cell components and tissue molecules. An important property of A1M, adding to its value as an antioxidant, is that the protein, after binding a maximum load of radicals, and/or reducing oxidants or oxidation products, does not present oxidative stress to tissue components. In other words, ROS, radicals and other oxidants are eliminated by A1M, hence A1M may be considered as a radical "sink". This feature may be of particular importance in damaged cells or other cells in which intracellular homeostatic processes are impaired and thus incapable of removing the oxidative stress that other antioxidants, as e.g. Vitamin E and D, impose on the cell after action.

Alpha-1-microglobulin

A1M is synthesized in the liver at a high rate, secreted into the blood stream and transported across the vessel walls to the extravascular compartment of all organs. The protein is also synthesized in other tissues (blood cells, brain, kidney, skin) but at a lower rate. Due to the small size, free A1M is rapidly filtered from blood in the kidneys. AIM has excellent anti-oxidative properties in general and specifically towards free haemoglobin; properties that makes it suitable for use in the treatment or prophylaxis of a variety of diseases that involves oxidative stress or wherein the presence of free haemoglobin induces or aggravates a disease or condition.

Alpha-1-microglobulin (A1M) is an endogenous antioxidant that provides antioxidation in several ways (FIG. 2B and figure legends hereto). Thus, the present invention relates to A1M which has been found to combine enzymatic reductase (category 1), non-enzymatic reduction (category 2) and radical-scavenging (category 3) properties. In addition, the non-enzymatic reduction mechanism (category 2) can be employed repeatedly with several cycles of electron-donation. Furthermore, the radical-scavenger mechanism (category 3) result in a net production of electrons further increasing the antioxidation capacity of the protein. In other words, the protein carries its own supply of electrons, is independent on cellular metabolism, and can operate both intra- and extracellularly. In addition, A1M can repair oxidative damage that has been inflicted to tissue components (a unique property assigned category 4). See also below for a detailed description of the radical scavenging mechanism.

A1M is a member of the lipocalin superfamily, a group of proteins from animals, plants and bacteria with a conserved three-dimensional structure but very diverse functions. Each lipocalin consists of a 160-190-amino acid chain that is folded into a β-barrel pocket with a hydrophobic interior. Twelve human lipocalin genes are known. Among the human lipocalins, A1M is a 26 kDa plasma and tissue protein that so far has been identified in mammals, birds, fish and frogs. A model of the three-dimensional structure of A1M is shown in FIG. 3. A1M is synthesized in the liver at a high rate, secreted into the blood stream and rapidly (T½=2-3 min) transported across the vessel walls to the extravascular compartment of all organs. The protein is also synthesized in other tissues (blood cells, brain, kidney, skin) but at a lower rate. A1M is found both in a free, monomeric form and as covalent complexes with larger molecules (IgA, albumin, prothrombin) in blood and interstitial tissues. Due to the small size, free A1M is rapidly filtered from blood in the kidneys. The major portion is then reabsorbed, but significant amounts are excreted to the urine.

Sequence and Structural Properties of A1M

The full sequence of human A1M was first reported by Kaumeyer et al. (5). The protein was found to consist of 183 amino acid residues. Since then, ten additional A1M cDNAs and/or proteins have been detected, isolated and/or sequenced from other mammals, birds, amphibians, and fish. The length of the peptide chain of A1M differs slightly among species, due mainly to variations in the C-terminus. Alignment comparisons of the different deduced amino acid sequences show that the percentage of identity varies from approximately 75-80% between rodents or ferungulates and man, down to approximately 45% between fish and mammals. A free cysteine side-chain at position 34 is conserved. This group has been shown to be involved in redox reactions (see below), in complex formation with other plasma proteins and in binding to a yellow-brown chromophore. Computerised 3D models based on the known X-ray crystallographic structures of other lipocalins suggest that Cys34 is solvent exposed and located near the opening of the lipocalin pocket (see FIG. 3). Complement factor C8γ, another lipocalin, also carries an unpaired Cys in position 34 that is involved in the formation of the active C8 complex.

In the present context the term "alpha-1-microglobulin" intends to cover alpha-1-microglobulin as identified in SEQ ID NO: 1 (human A1M) as well as SEQ ID NO: 2 (human recombinant A1M) as well as homologues, fragments or variants thereof having similar therapeutic activities. In a preferred aspect, the alpha-1-microglobulin is in accordance with SEQ ID NO: 1 or 2 as identified herein. In FIG. 19 is given the sequence listing of the amino acid sequence of human A1M and human recombinant A1M (SEQ ID NOs 1 and 2, respectively) and the corresponding nucleotide sequences (SEQ ID NOs 3 and 4, respectively).

As mentioned above homologues of A1M can also be used in accordance with the description herein. In theory A1M from all species can be used including the most primitive found so far, which is from fish (plaice). A1M is also available in isolated form from human, rat, mouse, rabbit, guinea pig, cow and plaice.

Considering homologues, variants and fragments of A1M, the following has been identified as important parts of the protein for the anti-oxidative effect:

Y22 (Tyrosine, pos 22, basepairs 64-66)
C34 (Cystein, position 34, basepairs 100-102)
K69 (Lysine, pos 69, basepairs 205-207)
K92 (Lysine, pos 92, basepairs 274-276)
K118 (Lysine, pos 118, basepairs 352-354)
K130 (Lysine, pos 130, basepairs 388-390)
Y132 (Tyrosine, pos 132, basepairs 394-396)
L180 (Leucine, pos 180, basepairs 538-540)
I181 (Isoleucine, pos 181, basepairs 541-543)
P182 (Proline, pos 182, basepairs 544-546)
R183 (Arginine, pos 183, basepairs 547-549)

(Numbering of amino acids and nucleotides throughout the document refers to SEQ ID 1 and 3, see also FIGS. 3 and 6; if other A1M from other species, A1M analogs or recombinant sequences thereof are employed, a person skilled in the art will know how to identify the amino acids of the active site(s) or site(s) responsible for the enzymatic activity.)

Human A1M is substituted with oligosaccharides in three positions, two sialylated complex-type, probably diantennary carbohydrated linked to Asn17 and Asn96 and one more simple oligosaccharide linked to Thr5. The carbohydrate content of A1M proteins from different species varies greatly, though, ranging from no glycosylation at all in *Xenopus leavis* over a spectrum of different glycosylation patterns. However, one glycosylation site, corresponding to Asn96 in man, is conserved in mammals, suggesting that this specific carbohydrate may be functionally important.

A1M is yellow-brown-coloured when purified from plasma or urine. The colour is caused by heterogeneous compounds covalently bound to various amino acid side groups mainly located at the entrance to the pocket. These modifications probably represent the oxidized degradation products of organic oxidants covalently trapped by A1M in vivo, for example heme, kynurenin and tyrosyl radicals (6-8, 10).

A1M is also charge- and size-heterogeneous and more highly brown-coloured A1M-molecules are more negatively charged. The probable explanation for the heterogeneity is that different side-groups are modified to a varying degree with different radicals, and that the modifications alter the net charge of the protein. Covalently linked coloured substances have been localized to Cys34, and Lys92, Lys118 and Lys130, the latter with molecular masses between 100 and 300 Da. The tryptophan metabolite kynurenine was found covalently attached to lysyl residues in A1M from urine of haemodialysis patients and appears to be the source of the brown colour of the protein in this case (6). Oxidized fragments of the synthetic radical ABTS (2,2'-azino-di-(3-ethylbenzothiazoline)-6-sulfonic acid) was bound to the side-chains of Y22 and Y132 (10).

C34 is the reactive center of A1M (9). It becomes very electronegative, meaning that it has a high potential to give away electrons, by the proximity of the positively charged side-chains of K69, K92, K118 and K130, which induce a deprotonization of the C34 thiol group which is a prerequisite of oxidation of the sulphur atom. Preliminary data shows that C34 is one of the most electronegative groups known.

Theoretically, the amino acids that characterize the unique enzymatic and non-enzymatic redox properties of A1M (C34, Y22, K92, K118, K130, Y132, L180, I181, P182, R183), which will be described in more detail below, can be arranged in a similar three-dimensional configuration on another frame-work, for instance a protein with the same global folding (another lipocalin) or a completely artificial organic or inorganic molecule such as a plastic polymer, a nanoparticle or metal polymer.

The three-dimensional arrangement of some of these amino acids (blue ovals, the lysines are depicted by a "+"), the A1M-framework (barrel), the electron-flow and the radical-trapping, are illustrated in FIG. 6.

Accordingly, homologues, fragments or variants comprising a structure including the reactive center and its surroundings as depicted above, are preferred.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred. Substitution of like amino acids can also be made on the basis of hydrophilicity, particularly where the biologically functional equivalent poly peptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids the hydrophilicity values of which are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Lle, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

In the present context, the homology between two amino acid sequences or between two nucleic acid sequences is described by the parameter "identity". Alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6.

Multiple alignments of protein sequences may be made using "ClustalW". Multiple alignments of DNA sequences may be done using the protein alignment as a template, replacing the amino acids with the corresponding codon from the DNA sequence.

Alternatively different software can be used for aligning amino acid sequences and DNA sequences. The alignment of two amino acid sequences is e.g. determined by using the Needle program from the EMBOSS package (http://emboss.org) version 2.8.0. The Needle program implements the global alignment algorithm described in. The substitution matrix used is BLOSUM62, gap opening penalty is 10, and gap extension penalty is 0.5.

The degree of identity between an amino acid sequence; e.g. SEQ ID NO: 1 and a different amino acid sequence (e.g. SEQ ID NO: 2) is calculated as the number of exact matches in an alignment of the two sequences, divided by the length of the "SEQ ID NO: 1" or the length of the "SEQ ID NO: 2", whichever is the shortest. The result is expressed in percent identity.

An exact match occurs when the two sequences have identical amino acid residues in the same positions of the overlap.

If relevant, the degree of identity between two nucleotide sequences can be determined by the Wilbur-Lipman method using the LASER-GENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20. In a particular embodiment, the percentage of identity of an amino acid sequence of a polypeptide with, or to, amino acids of SEQ ID NO: 1 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention is calculated in an analogous way.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and amino-acylating tRNA are known in the art. Transcription and translation of plasmids containing nonsense mutations is carried out in a cell-free system comprising an *E. coli* S30 extract and commercially available enzymes and other reagents. Proteins are purified by chromatography. In a second method, translation is carried out in *Xenopus* oocytes by microinjection of mutated mRNA and chemically amino-acylated suppressor tRNAs. Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. Naturally occurring amino acid residues can be converted to non-naturally occurring species by in vitro chemical modification. Chemical modification can be combined with site-directed mutagenesis to further expand the range of substitutions. Alternative chemical structures providing a 3-dimensional structure sufficient to support the antioxidative properties of A1M may be provided by other technologies e.g. artificial scaffolds, amino-acid substitutions and the like. Furthermore, structures mimicking the active sites of A1M as listed above and depicted in FIGS. 3 and 6 are contemplated as having the same function as A1M.

Diseases Associated with Oxidative Stress

In the following diseases or conditions are described which involve oxidative stress. It is contemplated that A1M can be used in the treatment of any of the diseases mentioned in the following.

Oxidative stress has been reported in a variety of diseases. As mentioned above, oxidative stress is a situation when there is an imbalance between free radicals and the protective antioxidants. Oxidative stress can induce a wide range of acute or long-term physiological reactions releasing various bio-active factors. These in turn can promote additional oxidation/free radical-formation which further accelerate the oxidative stress, etc. Thus, the physiological reactions and oxidative stress interact with each other as gears and together they make the oxidative stress machinery spin faster and faster (FIG. 5). Some of the more important gears are inflammation, ischemia and reperfusion, blood haemoglobin and environmental/food-derived factors, which will be discussed below.

A) Infection and Inflammation

Inflammation is a collective term for a wide range of secondary immune reactions to infections of all kinds, and that also characterizes several other diseases such as autoimmune diseases. The body responds to bacterial infections by recruiting white blood cells (monocytes and granulocytes) to the infection site. As described above, white blood-cells produce superoxide anions and hypochlorite. To obtain iron, many bacteria are hemolytic, i.e. they produce molecules, which induce rupture of red blood cells and exposure of haemoglobin to bystander tissue components. Furthermore, the inflammation is characterized by necrosis, i.e. cells at the infection site rupture and die. This leads to exposure of, for example, the mitochondrial respiratory enzymes that produce free radicals. Pro-inflammatory cytokines such as TNF-alpha, impair intracellular antioxidants, superoxide dismutase and glutathione peroxidase. In these ways, many factors contribute to oxidative stress during infection and inflammation.

An example of the diseases in this group is chronic obstructive pulmonary disease (COPD), an inflammatory lung disease. Inflammatory diseases of lungs and airways are associated with strong pathological oxidation of extravascular tissue. This is mediated by activation of neutrophil and eosinophil granulocytes and their secretion of peroxidases, as well as the challenge from molecular oxygen.

Arthritis is a group of diseases in which the joints are damaged in a way that involves inflammation. Arthritis can have many causes, for example forced trauma, bacterial infection, gout and autoimmune attack. The inflammation of the joints is associated with high levels of oxidative stress and oxidative modification of cartilage, connective tissue and cells.

Other examples of conditions with high levels of inflammation are

Autoimmune diseases (rheumatoid arthritis, thyroid diseases, etc)

Infectious diseases

Neurodegenerative diseases (Alzheimer's, Parkinson's, ALS, Huntingtons Disease, and Multiple sclerosis MS)

Inflammatory bowel diseases

Arthritis

B) Ischemia- and Reperfusion-Related Diseases

When the blood vessels are occluded or damaged, either permanent or intermittent, there is an increased formation of free radicals due to the cell-death resulting from the decreased blood-flow and hypoxia (ischemia). When blood-flow is restored (reperfusion) a sudden elevation of the local oxygen supply leads to a dramatic increase of ROS from reactions between cell-components and oxygen. For instance, the enzyme xanthine dehydrogenase, an essential and abundant component of DNA-metabolism, uses blood oxygen to form superoxide anions. If reperfusion is sustained over a long period, the formation of ROS exceeds the capacity of the endogenous antioxidants and oxidative stress occurs. Endothelial injury is induced by oxidative stress which in turn activates platelets and induce thrombus formation that further threatens to occlude the vessels.

Stroke is an ischemia-reperfusion-related condition of the brain caused by obstruction of the blood-flow, due to thrombosis, embolism, haemorrhage, etc. Infarction of an organ, e.g. heart, is a condition with tissue necrosis due to occlusion of the blood and ischemia-reperfusion effects. Atherosclerosis is a disease affecting arterial blood vessels. It is a chronic inflammatory response in the walls of arteries, partly due to the accumulation of macrophage type white blood cells and promoted by low density lipoproteins (LDL). Oxidative stress is a strong component in the development of atherosclerosis. Thus, oxidants and free radicals participate in oxidative modification of LDL, endothelial cell membranes and other components of the blood vessels. Oxidized LDL (ox-LDL) binds to specific receptors in the endothelium and local accumulation of ox-LDL leads to recruitment of monocytes which differentiate to macrophages at the specific site. This leads to inflammation, attraction of granulocytes and an increased local production of ROS from NADPH-oxidase, MPO and other sources. The local endothelial damage, resulting in atherosclerotic plaques, ultimately occludes the blood flow.

Arteriosclerosis

Ischemic heart disease

Stroke and other conditions secondary to ischemia

Hypertensive disorders

Metabolic disorders (diabetes, dyslipedemia, hypercholesterolemia)

Iatrogen ischemia- and reperfusion-related damages are developed secondary to the treatment of an underlying disease. During the treatment the different gears shown in FIG. 5 may drive the oxidative stress.

For example, several methods of dialysis are in practice to replace lost kidney function. The very complex functions of the kidneys can be summarized as maintaining water and salt balance of the body and removing harmful and toxic degradation products. The kidneys operate by continuous filtration of the blood, followed by an active reabsorption of most components, including adequate amounts of water, and excretion of excess water, salt and toxic degradation products. Free radicals and ROS, especially small free organic radicals, such as urate and 3-hydroxy-kynurenine, are examples of toxic substances normally cleared from blood by the kidneys. Dialysis is far from a perfect replacement of the kidneys, and dialysis patients thus suffer from oxidative stress. In addition, it has been shown that the dialysis process itself induces an inflammatory response also contributing to the oxidative stress. Hypothetically, the higher incidence of atherosclerosis among dialysis patients may therefore be explained by the oxidative stress associated with kidney failure and the dialysis process.

Ischemic heart patients undergo by-pass operation on a routinely basis. During surgery, a heart-lung machine pumps the blood. During this time, many of the red blood cells are being destroyed which results in free haemoglobin, a potent oxidizer as described above. Furthermore, coronary heart surgery as well as other vascular surgery, requires that the blood flow is stopped during the procedure. When the blood flow again is established, reperfusion damage occurs.

Cell and organ transplantation. One of the problems encountered in cell and organ transplantation is that ROS are being formed in organs and cells during storage. The situation resembles the problems encountered during ischemia-reperfusion. This oxidative stress can be prevented or at least decreased in animal models by use of ROS scavengers. Much effort has been spent on trying to optimize the medium used to store and transport solid organs used for transplantation. Cold salt solutions with nutrients designed specifically are being used today for this purpose. However, allowed ischemia time (time without oxygen) is still very limited for organs like heart, lungs, kidneys and liver. Increasingly, pancreatic islet cells and different kinds of so-called stem cells (hematopoietic and mesenchymal dito, for instance) are also transported around the world for transplantation purposes. Along the same lines, transplantation of retinal tissue is a future potential treatment currently tried in animals. Diseases characterized by oxidative damage of the retina are often indications to retina transplantation. It was recently shown that pre-conditioning of the retinal tissue can protect it against oxidative cell death.

The examples thus include:

Use of kidney dialysis

Use of heart and lung machine

Vascular surgery

Cell and organ transplantation

C) Oxidative Stress as a Result of Free Haemoglobin, Heme and Iron Ions

As described previously, free haemoglobin and its metabolites are among the strongest endogenous oxidants. Several protective antioxidative enzymes and protein systems exist naturally to prevent oxidation. In many diseases bleeding is part of the pathophysiology, enhancing the oxidative stress. Iatrogenic causes are also common. Bleeding can occur either systematically or within closed compartments, i.e. bleedings intra-cranially, within joints, in the gastrointestinal tract and within capsulated organs.

Haemolysis, uncontrolled destruction of red blood cells, may lead to haemoglobinemia and haemoglobinuria, i.e. elevated concentrations of haemoglobin in the blood and urine, respectively. Plasma haemoglobin is filtered through the glomeruli of the kidneys and re-absorbed by tubular cells where it may lead to formation of precipitates called hemosiderin during conditions with haemoglobin overload, causing oxidative damage. If the haemoglobin overload is too high and no treatment available, the kidneys are irreversibly damaged and dialysis or kidney transplantation required.

Diseases in which red blood cells lyse are categorized by the location of the lytic event, either inside the blood vessels or outside them. Both intra- and extravascular hemolysis causes anemia that can be divided into different categories depending on the cause of lysis. Thus, three main groups of autoimmune haemolytic anaemia (AIHA) are warm IgG-mediated AIHA, cold IgM-mediated AIHA or cold agglutinin syndrome and drug-induced immune haemolytic anaemia. In all of these diseases antibodies made by the patient coat and destroy the red blood cells. Another special form of antibody-mediated hemolytic anemia is found in fetuses/newborns to mothers who have been immunized to make blood group antibodies against the paternal antigens on the red cell surface in the offspring. Hemolytic disease of the newborn is a potentially lethal disease since it can lead to dangerously low haemoglobin values and eventually hydrops fetalis, a critical state in which the baby accumulates water because of the relative lack of red blood cells able to circulate haemoglobin.

Many different enzyme defects of the red blood cell metabolism can also be associated with hemolytic syndromes. Mechanical hemolysis and paroxysmal nocturnal haemoglobinuria (PNH), an acquired intravascular hemolytic disease due to lack of glycosylphosphatidylinositol-anchored complement regulatory proteins, represent other less common forms of intravascular hemolysis. Furthermore, immediate or delayed hemolysis may occur as adverse events following clinical transfusion or transplantation (see below). Patients with myelodysplastic syndrome and dyserythropoeitic anemia may also suffer from ineffective RBC production and subsequent lysis. In addition to conditions associated with an excess of free haemoglobin, patients with iron metabolism disorders including hemochromatosis suffer from increased oxidative stress and like patients with hemolytic disease may benefit from upregulated antioxidative mechanisms.

Both heme and free haemoglobin resulting from these hemolytic conditions are associated with generation of various reactive oxygen species (ROS) which can induce oxidative damage to matrix molecules, cell membranes and other tissue components as outlined above. Especially intravascular hemolysis results in unacceptably high concentrations of free haemoglobin in plasma which can lead to hypertension, kidney damage and circulatory collapse. This can be seen in its most dramatic and potentially lethal form as part of acute hemolytic transfusion reactions following administration of a blood unit with the wrong ABO group. The whole situation is characterized by an immunological induction of an oxidative stress response. For instance, the supply of haemoglobin-binding haptoglobin in plasma is rapidly superseded since complexes between haemoglobin and haptoglobin are rapidly cleared from the circulation by the CD163 receptor. Accordingly, lowered or absent haptoglobin in plasma is used as a diagnostic marker for hemolysis. Similarly, free heme is bound by hemopexin in plasma from which this complex is then removed by interaction with the CD91 receptor.

Infections are yet another type of diseases that can lead to hemolysis. In malaria, red blood cells are invaded by the parasite *Plasmodium*, which feed, multiply and intermittently cause the cells to rupture. Parvovirus B19 attaches via the P blood group antigen to erythroid progenitor cells and infects them preferentially. In children, such an infection is not seldomly characterized by production of auto-anti-P which causes red blood cell destruction. Similarly, a *Mycoplasma* infection raises an antibody response that often cross-reacts both with the pathogen and the I blood group antigen, thus causing intravascular lysis that can sometimes be life-threatening.

Another group of diseases with a hemolytic component is found in large numbers of people around the globe. There are multiple variants of genetic disorders of haemoglobin but a few of the most important will be mentioned here: Sickle cell anemia, in which a mutation of haemoglobin resulting in the HbS variant, is associated with malformation and destabilization of red blood cells, especially if the oxygen tension drops. Thalassemia is another collection of genetic disorders reducing synthesis of haemoglobin and sometimes leading to hemolysis. Both sickle cell patients and thalassemics have been shown to suffer from iron overload, inflammation and oxidative stress. Interestingly, another lipocalin member, NGAL, has recently been shown to be upregulated in thalassemic patients in which oxidative stress is known to be increased. These kinds of disorders lead to exposure of haemoglobin and the downstream events described above: formation of ROS, free heme, free iron, oxidative stress and vasoconstriction.

Iatrogenic Conditions Associated with Cell-Free Haemoglobin.

Blood transfusion. When red cells from a blood donor are transfused to a patient, storage of the blood unit has taken place at 4 degrees for a maximum of 42 days. This results in suboptimal function and stability of the cellular elements in the plastic bag. For instance, even if there are regulations to ensure an optimal quality of the blood components transfused, a certain amount of haemoglobin leakage from the cells is unavoidable and expected. There is also a progressive oxidation of cytoskeletal proteins and accumulation of denatured haemoglobin in stored red cells. In addition, a fair percentage of damaged cells will be lysed or cleared immediately from the circulation of the recipient upon infusion. Thus, even if the best possible matching of blood groups is ensured by crossmatching etc at the blood center, the recipient will suffer an increased load of free haemoglobin following transfusion and consequently also the negative effects of oxidative stress.

Despite this, almost half a million blood units are given in Sweden annually and accordingly millions around the globe. Today transfusions are considered a prerequisite for modern medicine, including surgical procedures, safe obstetrical activities, hematopoietically suppressing aggressive chemotherapy treatment for cancer, as well as stem cell or organ transplantation.

Blood substitutes. Since the need for transfusible blood continuously is exceeding the actual supply, there is a constant demand for alternative sources of blood. Several blood substitute products are in clinical trial today, in North America as well as Europe and Sweden. A major group of blood substitutes are the haemoglobin-based oxygen carriers (HBOCs). These consist of concentrated solutions of cell-free haemoglobin, modified in one way or another to minimize the adverse effects of the haemoglobin molecule (see above). Although no HBOC is used clinically today, it is believed that it is only a question of time before treatment with blood substitutes is a reality for indications such as haemorrhagic shock induced by trauma and prevention of hypotension.

In addition to the above-described situation of blood transfusion at its best, there are three situations in which the burden of free haemoglobin and heme (and consequently oxidative stress) risks to be further increased:

1) Current statistics from haemovigilance (i.e. blood surveillance) systems in most developed countries today show clearly that the most frequent serious incidents associated with blood transfusion are blood-group-related. For instance, this applied to >80% of all serious incidents in the Serious Hazards of Transfusion (SHOT) database in the UK. In addition, blood transfusions that are ABO-mismatched by mistake can cause intravascular hemolysis and lethal adverse reactions due to acute overload of free haemoglobin in plasma and all its downstream effects. This tragic complication has been shown to account for as much as 50% of all transfusion-related fatalities. If the patient makes it through the acute phase of the haemoglobin overload reaction, it is not unlikely that permanent kidney damage persists and may be a reason for kidney transplantation later on. All these reactions are due to lack of appropriate ways to take care of the excessive amounts of free haemoglobin, heme and cell membranes left behind following this kind of lytic episode due to the naturally-occurring anti-A and/or -B present in the plasma depending on the recipients ABO blood group. Even if less common, also other mismatched blood group combinations outside the ABO system can cause intravascular or extravascular hemolytic events that put the patient at risk. Most importantly, blood units are only matched for ABO and RhD status today which leaves the other approximately 300 blood groups unmatched. If the patient has or mounts an immune response against any of those structures, then hemolysis may occur without the need for a mistake to have happened in the transfusion process.

2) Patients with chronic transfusion needs will eventually suffer from iron overload since the transfused red cells will have a shorter half-life in the circulation of the recipient. This is due to many factors but the storage lesion is typically considered important and the disease for which the patient was transfused can also cause increased turnover of red cells in general. Thus, these patients are treated with chelating agents with the capacity to bind iron ions, thereby lowering the oxidative stress. However, there is no specific treatment to take care of the increased load of heme and haemoglobin associated with chronic transfusion, nor the oxidative stress in general caused by the combination of a lytic disorder like e.g. thalassemia major and the chronic transfusion need it creates.

3) Finally, patients requiring irradiated blood components receive red cell units that are further damaged beyond the standard storage lesion. Typically, a dose of gamma-irradiation at 25 Gray is delivered to each blood unit to ensure that all cellular components are inactivated, i.e. not able to divide and proliferate. This is critically important for any patient whose immune system is seriously suppressed or non-funcational. Accordingly, common patient categories receiving this kind of blood includes stem cell transplant recipients, patients treated with certain chemotherapeutic agents, fetuses transfused in utero and patients with serious congenital immune defects.

The examples thus include:
Hemolytic disorders
Infections disease (malaria, *shigella*, hemorragic fevers etc)
Metabolic disease (sickle cell anemia, thalassemia, hemolytic uremic syndrome etc, hemophilia)
Blood transfusion
Treatment with blood substitute
Anti-coagulation therapy (detta berörs ej)
Per- and post-operative complications (detta berörs ej, kan vara per och postoperative blödningar som hindrar eller förd röjer läkning)

D. Oxidative Stress as a Result of Environmental and Food Derived Factors

Ultraviolet (UV) light, or photon-irradiation, has been known for a long time to induce free radicals and oxidative stress, and thus damage of the tissues (i.e. skin) exposed to UV-light. The mechanisms include direct damage by the UV-irradiation of cellular DNA and indirect damage via formation of ROS that cause tissue damage by oxidative modification. The latter is called photo-oxidative stress.

Iatrogenic causes are again important in this respect. Treatment of infections with antibacterial and viral therapies can cause inflammation and formation of oxidative products that tip the balance (FIG. 1). Moreover, aggressive cytostatic cancer therapies induce massive cell-death which in turn drain the endogenous ant ioxidative systems. Furthermore, radiation therapies induce large amounts of free radicals. Likewise, charged particle irradiation of living tissues can induce biological responses ranging from necrotic cell-death, apoptosis or cell-cycle arrest to oxidative stress induced by ROS-formation. Ion-irradiation therapy, or charge particle microbeam irradiation, is a particular form used for treatment of cancer. For example, in proton-irradiation therapy an irradiation dose is targeted to a tumour, and the irradiation doses used are high enough to kill the tumour cells but low enough to minimize oxidative damage to surrounding tissue via ROS-formation. The examples include:
UV light irradiation
Anti-infection therapies (anti-bacterial, viral and parasites)
Cytostatics
Radiation therapy
X-ray Environmental pollutions and toxins have a general negative effect on all living creatures. Depending on the antioxidative capacity of an individual, it has a varying degree of natural resistance to oxidative stress. Rats and cockroaches have extremely high antioxidative capacity, therefore they have a high predictive survival rate in extreme events like post nuclear war situations etc.

The majority of the human antioxidative capacity is endogenous, however the different systems depend on co-factors such as vitamins and minerals, provided by food intake. The nutritional status of an individual is therefore important to counteract oxidative stress. Antioxidative therapy, with supplementation of vitamin C and E, have been evaluated in many situations but since the effects requires that the reduced products are removed from the body, there are no studies that support their use in situations with high oxidative stress (e.g. preeclampsia).

E. Oxidative Stress-related Disorders of the Skin.

The skin is the largest organ of the body and provides a physical barrier that protects the human organism from the environment. Pathological conditions involving disruption of the barrier function easily develops inflammation due to oxygen-exposure, UV-light irradiation, microbial invasion, etc. Furthermore, inflammation and other oxidative stress-related disorders of the skin have characteristic features due to its high content of ECM components, for example collagen fibers. Collagen is especially sensitive to oxidative damage since this molecule has an extremely slow turn-over rate. In fact, the collagen fibres of the skin are made to last a life-time. Thus, the number of oxidative modifications in skin tissue increases over time, with age.

Atopic dermatitis is a chronic (relapsing) inflammatory condition of the skin caused by physical and chemical irritation (e.g. allergy) leading to flaky skin and eczema. Psoriasis is a similar condition but is caused by autoimmunity instead of outer irritants.

Chronic leg wounds and other chronic ulcers are characterized by a persistent inflammation due to impaired blood flow, commonly seen in diabetic patients, bleeding and/or microbial infections. Several mechanisms are believed to cause the defective healing. Haemoglobin, heme and free iron, originating from red blood cells, migrating from blood to the wound tissue, as well as from extravascular necrosis, are important pathogenic factors. The ROS and free radicals induced by the haemoglobin degradation components present strong oxidative stress that leads to tissue damage and cell destruction and therefore prevents normal healing.
UV-light irradiation
Age-related modifications
Acute wounds
Chronic skin wounds
Atopic dermatitis
Psoriasis F. Oxidative Stress and Reproduction The female reproductive tract is of particular interest from an oxidative stress point of view. During the normal menstruation cycle, there is a monthly bleeding, discharging the endometrium. Many women experience pain in this process, so called dysmenorrea. We have recently been able to detect high levels of marker for oxidative stress in plasma from these women (unpublished data).

Dysmenorrea can also be a symptom of endometriosis, still an enigma within the field of gynecology. In this condition, there is an ectopic endometrial tissue spreading as islands in the abdominal cavity. These islands react to the systemic hormone levels and consequently bleed during menstruation. The intra-abdominal blood cause pain and later also bried formation, strings may occlude the intestine as well as the uterine tubes causing infertility and gastrointestinal problems.

Implantation is when the fertilized egg establishes contact with the pregnant endometrium, thedecidua. Regulation of the uterine blood flow is important both during both menstruation, implantation and during pregnancy. Monoamines are potent vasoactive mediators that regulate blood flow and, in the case of histamine, capillary permeability. Serotonin and histamine play a role in decidualization, implantation and, in the case of histamine, also in immuno-modulation. It has been reported that local injury to the endometrium, caused by taking a biopsy, increased the incidence of implantation in IVF (in vitro fertilization) patients. Thus, it is likely that inflammatory mediators, including histamine, which are normally released during tissue repair and remodelling function as mediators of decidualization and implantation. Implantation in rats was also induced by histamine when combined with suboptimal doses of estrogen while intrauterine application of inhibitors or antagonists to histamine receptors inhibits decidua formation. The oxidative stress that follow the regulated inflammation, may in the case of infertility exceed the antioxidative system and thereby cause miscarriage.

Preeclampsia (PE) is a two-stage disease. The first stage, implantation and placentation, is characterized by a defect invasion of the placental cells, trophoblasts, into the muscle layers of the spiral arteries of the endometrium. This contributes to a reduced utero-placental blood flow that results in reduced oxygen delivery and intra uterine growth restrictions (IUGR) seen in one of four PE cases. A growing body of evidence suggests that this oxidative stress causes release of placental factors that in stage two give rise to general endothelial damage and inflammation. We have shown involvement of genes in both oxidative stress and inflammation. Of particular interest is Hb α2 and γ transcripts that were significantly over-expressed in placentas from women with PE versus normotensive pregnancies. In fact, we have recently been able to show significantly increased levels of free haemoglobin, in maternal plasma and urine from PE patients (not shown). Our working hypothesis is that the local HbF-upregulation in placenta is an oxidative insult that triggers leakage of the placenta barrier and hemolysis of maternal erythrocytes. Once the blood-placenta barrier is damaged, fetal cells and fetal haemoglobin may enter the maternal circulation, causing vascular inflammation that characterize stage two in PE. The resulting increase of maternal free haemoglobin is a major cause of hypertension, kidney failure and eclampsia, the hallmarks of PE that includes all the gears in the oxidative stress machinery (FIG. 5).

Premature contractions and delivery are common obstetrical problems. The essential mechanism that triggers premature cervical ripening and uterine contractions is inflammation. The inflammation can be induced by infections and bleedings. Oxidative stress is likely the main culprit also in these situations.

Dysmenorrea
Endometriosis
Preeclampsia
Premature labour

G. Oxidative Stress in Neonatal Medicine

A high percentage of all deliveries are premature, i.e. before gestational week 34. Extreme prematurity (gestational week 23-28) is often complicated with severe organ damage. Dominating problems in premature babies are lung damage, necrosis of the gastrointestinal tract, cerebral hemorrhages and infections, situations characterized by high oxidative stress. Accordingly, oxidation is the damaging denominator. The endogenous antioxidative systems are not fully developed and/or mature to handle the oxidative stress occurring outside the womb. In normal pregnancies the lungs, skin and the gastrointestinal tract of the baby, are all protected by the amniotic fluid surrounding the fetus from both the inside and outside, i.e. to the skin.

Intraventricular haemorrhage (IVH). Severe cerebral IVH occurs in about 15% of preterm infants delivered below 28 gestational weeks. Over 50% of infants with IVH develop post-hemorrhagic hydrocephalus and 40% develop severe neurological impairment (mainly cerebral palsy) as detected at 2 y of age. There is no available therapy to prevent infants from developing either hydrocephalus or serious neurological disability. Haemolysis of extravasated blood causes release of free haemoglobin in to the intraventricular cerebro-spinal fluid (CS F). Free haemoglobin and its degradation products heme, CO and free iron are highly capable of inducing oxidative stress and pro-inflammation. The pre-oligodendrocytes populating the periventricular white matter are extremely vulnerable to inflammation and oxidative stress resulting in damage to cortico-spinal white matter tracts leading to development of cerebral palsy. Secondary oxidative stress arises from the cell death induced by haemolysis products and leads to release of oxidants and free radicals mainly from damaged mitochondria, adding to the oxidative stress caused by free haemoglobin itself. The examples include:

Respiratory distress
Intraventricular brain haemorrhage
Necrotic enterocolites (NEC)
Infections
Hemolysis Principles of Administration of Alpha-1-Microglobulin From the description above, it follows that A1M must be present for a sufficient period of time in a fluid, organ, buffer, etc, to prevent, or inhibit, the actions of an oxidant present in the same biological specimen. On the other hand, A1M can also be used at a single occasion for cleaning-up purposes, i.e. to remove an oxidant or an oxidation product. Therefore, medical applications of A1M can be of two major types, 1) continuous in a defined period of time or 2) single/multi-dose. Mostly, single-dose applications will be used for practical reasons but continuous administration is also possible, for instance by using recombinant A1M-producing vehicles (i.e. cells).

A second categorization is related to the location of the A1M administration, i.e. A1M can be added 1) globally/systemically or 2) locally. Examples of category 1) is artificial dialysis, where A1M can be used for radical scavenging as an addition to the full volume of dialysis fluid, or atherosclerosis treatment, where A1M can be added to the blood to repair MPO-induced endothelial damage. Examples of category 2) is treatment of chronic wound legs, where A1M can be added in a single-dose locally to the wound to "clean up" deposited heme and radicals, and to repair oxidation products.

The administration of A1M may be once daily or divided in multiple doses daily dependent on the particular disease to be treated, the condition of the subject to be treated (age, weight, severity of the disease). A daily dosage of A1M is normally from 0.5 mg/kg body weight to 100 mg/kg body weight. The dosage regime depends on the disease or condition to treat and may involve treatment for 1 minute up to life-long treatment.

A composition typically comprises from 10-99% w/w of A1M but may be less than 10% as low as trace amounts, if pharmaceutically feasible. For additional details and examples of formulations, please see below under formulation examples.

A1M is preferably administered in the form of a pharmaceutical composition. Due to the polypeptide nature of A1M the preferred compositions are designed for parenteral use, but A1M may also be applied locally e.g. on the skin in connection with healing of wounds, in joints in connection with arthritis, or in the brain cavities when treating intraventricular hemorrhages. Moreover, as it appears from the description herein A1M can also be added to blood intended for transfusion or to cells or organs to be transplanted into a subject. Accordingly, A1M can be formulated in a liquid, e.g. in a solution, a dispersion, an emulsion, a suspension etc., or it may be in a formulation suitable for administration to the skin such as, e.g., a lotion, a cream, an ointment, a suspension, an emulsion, a paste, a powder, a patch, a plaster, a dressing, a soap, a shampoo, sun protection lotion etc. Moreover, A1M may be included in medical devices or equipment, e.g. as a releasable coating on catheters etc.

Alternatively and in addition, specific carriers to target the active substance to a specific part of the body can be included. For example an antibody-A1M complex where the antibody is targeted to the locality of choice ("homing") by its specificity for a certain epitope; a stem cell or a recombinant cell with such homing properties, e.g. integrin-receptors specific for a tissue and with the artificial or natural capacity to secrete large amounts of A1M. The treatment would be more efficient since the drug would be concentrated to the site of inflammation, bleeding, etc, and less A1M would be required.

For parenteral use suitable solvents include water, vegetable oils, propylene glycol and organic solvents generally approved for such purposes. In general, a person skilled in the art can find guidance in "Remington's Pharmaceutical Science" edited by Gennaro et al. (Mack Publishing Company), in "Handbook of Pharmaceutical Excipients" edited by Rowe et al. (PhP Press) and in official Monographs (e.g. Ph.Eur. or USP) relating to relevant excipients for specific formulation types and to methods for preparing a specific formulation.

Examples of Possible Uses for Alpha-1-Microglobulin as Therapeutics

Examples presented below are solely included for inspiration and shall not in any way be considered as limiting.

Due to its unique properties as discussed herein, A1M may be significantly superior to presently known alternatives as treatment in a number of applications. The main principle for the below listed applications is that A1M is added to a clinical situation either before an expected increase in oxidative stress, during or after a situation with high oxidative stress, in order to counterbalance the oxidation. Many clinical situations characterized by high oxidative stress are listed under the bullets above, only a selection of diseases are used in the examples below, but the treatment principles apply to all. An overview is given in the following Table 1.

TABLE 1

Conditions with oxidative stress that can be treated with A1M

| GROUP | DISEASES/ CONDITIONS | IATROGEN CONDITIONS |
|---|---|---|
| A. Infection and inflammation | Lung (COPD) Autoimmune inflammations Neurodegenerative inflam Inflam. bowel disease Arthritis, arthrosis | |
| B. Ischemia-and reperfusion-related | Atherosclerosis Stroke Myocardial infarction | Dialysis Organ transplantation Stem cell transplantation Heart-lung machine stress |
| C. Oxidative stress as a result of free haemo-globin, heme, and iron ions | Hemolytic diseases Hemochromatosis Malaria inf. Shigella inf. Hemorrhagic fevers Sickle-cell Thalassemias | Blood transfusion Treatment with HBOCs |
| D. Environmental or food-derived factors | UV-light irradiation | Cancer radiotherapy Radiation therapy Anti-infection therapy X-ray investigation |
| E. Skin | UV-light irradiation of skin Atopic dermatitis Psoriasis Chronic leg wounds Acute wounds Ageing | Wound healing after surgery, including plastic surgery |
| F. Reproduction | Dysmenorrea Endometriosis Infertility Preeclampsia Pre-term deliveries | |
| G. Neonatal conditions | Brain hemorrhages including IVH Hemolytic conditions Respiratory distress Necrotic enterocolitis | |

A) Infection and Inflammation

A1M could be given in combination with conventional drugs against infection and anti-inflammatory drugs in order to counteract the oxidative stress seen in for example COPD. In this disease, A1M could be used as an addition to lung lavage fluid or as inhaled aerosols. The effect of A1M in this application would be to scavenge radicals and reduce/repair oxidative modifications in lung tissue. The treatment can be of single- or multidose type and local and the effect pro- and interactive.

B) Ischemia- and Reperfusion-related Diseases

Atherosclerosis. As describe above, it is well established that oxidants and oxidative stress are central in the development of atherosclerosis, and that oxidation of LDL is a common intermediate leading to atherosclerotic plaques. Although most studies of antioxidants have failed to show protective effects against the disease, we see A1M as a potential therapeutic agent for several reasons: 1) it has a broad antioxidant arsenal: enzymatic and non-enzymatic reduction of oxidants and radical scavenging; 2) it has an oxidation repair capacity of potential importance to atherosclerotic lesions; 3) A1M can inhibit oxidation of LDL by heme and ROS (not shown); 4) A1M can reduce heme- and ROS-induced oxidative modification of LDL (not shown); 5) A1M is present in endogeneous LDL-particles (not shown), suggesting that it has a role as an antioxidant in LDL already and that atherosclerosis is a result of pathological oxidation in excess of the capacity of A1M; 6) A1M participates in de-activation of MPO (not shown). Application of A1M for prevention and/or treatment of atherosclerosis can be continuous and global, using for instance venous infusion or transplantation of a cellular vector with high A1M-producing capacity. Alternatively, the treatment may be of single-dose type and local, for example by direct infusion into a cardiac coronary artery. The treatment can be pro- or interactive, inhibiting LDL-oxidation and atherosclerosis formation, or therapeutic repairing/removing atherosclerotic plaques.

Stroke and heart infarction are indications where A1M can be used to inhibit oxidative stress and repair lesions induced by the ischemia-reperfusion events. A1M could be added systemically or locally. The treatment can be of single-dose, multi-dose type or continuous and the effect post-active. In the case of myocardial infarction the A1M-treatment could be combined with surgical invasive procedure associated with arterial distension, etc.

Arthritis. In these inflammatory conditions, treatment of A1M is favourable because of the natural limitation of the disease site(s). Mechanistically, the anti-inflammatory, repair and ECM-promoting properties would be especially valuable in the treatment. The treatment can be of single-dose, multi-dose type or continuous and the effect post-active.

Dialysis. Oxidative stress induced as a result of dialysis can be prevented by A1M-treatment and oxidative damage induced by dialysis is repaired by A1M. Two major types of clinical dialysis exist: hemodialysis and peritoneal dialysis. In hemodialysis, the patient's blood is circulated extracorporeally through a dialysis apparatus where it is equilibrated with a dialysis fluid over a semipermeable membrane. A1M can be added to the dialysis fluid in a way that does not allow it to enter the blood. The A1M will reduce and bind oxidants/radicals, and thus function as an oxidant- or "radical sink" that traps and eliminates the radicals and oxidants, increasing the rate of elimination of radicals ten-fold. Alternatively, the blood can be passed through a column of insolubilized A1M, arranged on-line with the dialysis apparatus. In peritoneal dialysis, the dialysis fluid is injected into the peritoneal cavity of the patient (surrounding the intestines), and left there for a time-period. The peritoneum acts as the dialysis membrane allowing small molecules (water, salts, small organic solutes including radicals) to equilibrate. The dialysis fluid is then drained and discarded. Also in this case, A1M can be added to the dialysis fluid in a way that does not allow it to enter the blood and A1M will function as an oxidant- or radical-"sink". Thus, the mode of application of A1M is single-dose (although repeated for each round of dialysis), local and pro-active.

Organ transplantation. Since oxidative cell and organ damage is known to be a limiting factor among others in the field of transplantation, we propose to add A1M to rinsing solutions and cold storage media to increase the viability and transportation time of such cells and organs. This would include all organs being used routinely for transplantation (e.g. heart, lung, liver, intestines, pancreas, kidney, skin, bone, retinas) and also cells (e.g. pancreatic cell islands, mesenchymal stem cells, haematopoietic stem cells, dendritic cells and leukocytes for donor lymphocyte infusions to treat graft-versus-host disease).

C) Oxidative Stress as a Result of Free Haemoglobin, Heme and Iron Ions

Hemolytic diseases. As described above there are multiple different diseases characterized by uncontrolled lysis of red blood cells, intra- or extravascularly. Especially those involving intravascular hemolysis would be an interesting target for A1M therapy in that the problem includes free haemoglobin and heme in plasma. These diseases include autoimmune hemolytic anemia of the cold IgM-mediated type, paroxysmal nocturnal haemoglobinuria, and paroxysmal cold haemoglobinuria. The treatment is envisioned to be a single or multiple (possibly continuous) intravenous administration of A1M in a therapeutic fashion. These patients often have no remaining haptoglobin levels and therefore have no buffering defense to bind the free haemoglobin.

At the same time, we know that patients with extravascular hemolysis, e.g. diagnoses including autoimmune hemolytic anemia of the warm IgG-mediated type and drug-induced hemolytic anemia, have impairment of their kidney functions. It is likely that they also suffer from increased oxidative stress based on the large amounts of haemoglobin and heme they have to process when their reticuloendothelial system including macrophages in the spleen phagocytose billions of extra red blood cells compared to steady state. It is possible that also these patients could benefit from antioxidative therapy by A1M.

Blood transfusion. Our preliminary data show that A1M prevents hemolysis (FIG. 9) and protects red blood cells from already formed free heme/haemoglobin in vitro. At the same time, today's storage solutions for red blood cells for transfusion do not take into account the problem with oxidative damage during storage. We have therefore performed experiments in which A1M was added to blood tubes or even to the storage medium of whole blood units (not shown).

Improvement of the quality of red cell units: As a preventive measure to increase the quality of red blood cells for transfusion we therefore propose to add A1M before and/or after storage, depending on what kind of blood component it is. This would be a pro-active, single-dose scheme for each blood unit. Optimally, A1M would be added to the storage medium although this is currently difficult due to the heating procedures which are used to sterilize it. Thus, A1M could be added separately 1) before storage period is started (prophylactic); 2) as a rejuvenation agent after a certain time period had passed (interactive); or 3) prior to issuing the blood unit to the ward ("clean-up"/"therapeutic" approach). The purpose would be to be able to supply patients with a better blood component by the addition of suitable doses of a non-immunogenic, endogenous protein. It would be especially appealing in the situation of gamma irradiation of blood since those units tend to be more damaged than common blood for transfusion.

Therapy in the event of an acute or delayed hemolytic transfusion reaction: Yet another application of A1M in relation to transfusion of different blood components (red cells, platelets and plasma) is to treat patients who have suffered a hemolytic transfusion reactions following the administration of one or more incompatible unit(s). Currently, there is no specific treatment to avoid the toxic effects of free haemoglobin which result from antibody-mediated lysis of red blood cells. All available therapies are unspecific, broad and not very successful due to the fact that they do not target the problems, free haemoglobin and heme in plasma as well as the general oxidative stress they create. Instead, the traditional pharmaceutical approaches have been to counteract the biological effects of these substances. We propose to use A1M as an addition to steroids, adrenaline and other agents in the current therapeutic arsenal. The lysis can be of one of two types: 1) active which means that incompatible donor red blood cells are transfused, get coated with the recipients antibodies and lysed, either intra- or extravascularly; and 2) passive which occurs when the patient's own red blood cells are lysed due to the administration of incompatible plasma containing naturally-occurring anti-A or -B. This scenario is less dangerous than 1) but can occur after transfusion of both plasma units and platelets. Whilst plasma is always supposed to be given in a compatible way mistakes can occur here as well as in 1). However, for platelets it is common to give O platelets to patients of all blood groups which means that high-titer anti-A and -B can be transferred to the patient and cause hemolysis even if this is not due to a mistake.

Blood substitute treatment. A1M can be administered as an addition to the HBOC itself, either in free form or as a fusion-protein with the HBOC to decrease further any possible adverse effects of extracellular haemoglobin.

Thus, we propose to give A1M to patients as a means of coping with the negative consequences and oxidative stress induced by free haemoglobin and heme. A preferable method is intravenous administration of protein as soon as possible after the incident (when the mistake has been noted, or if the patient starts passing red urine or complains about symptoms like back pain, fever, sweating and nausea). This would be a single or multiple dose therapeutic application. Other non-specific treatments like steroids, adrenaline and forced diuresis would still have to be tried.

A1M may be applied in therapy to prevent oxidative stress due to iron overload following transfusion or in the case of hemochromatosis, Wilson's disease (copper ion over load) and other similar diseases in which metal ions are being accumulated in the patient's body. In chronically transfused patients or other states accumulating metal ions, we propose to supplement the chelation therapy (by which divalent ions are bound be an infused substance) with A1M infusions to decrease the oxidative stress that has been documented in these patients.

D) Oxidative Stress as a Result of Environmental and Food-Derived Factors

Targeted cancer radiotherapy. Cancer can be treated with irradiation the purpose of which is to kill the tumour cells. The irradiation can be targeted, i.e. more or less focused on the tumours. A problem with this is, of course, that healthy tissue is also affected. For this reason, the dose has to be kept low, limiting the effect of radiotherapy. Here, A1M can be used to prevent destruction of bystander cells and tissue components, allowing a much higher irradiation dose to be used. The application of A1M is single-dose, local and pro-active.

E) Oxidative Stress-Related Disorders of the Skin

UV-irradiation. A1M can be used to prevent UV-irradiation-induced tissue damage. Since parts of the damage are mediated by oxidative stress, the combination of antioxidation-, radical scavenging-, oxidation repair- and "radical sink"-properties of A1M makes the protein a unique and powerful agent to minimize tissue damage during UV-light irradiation. For example, A1M can be employed as a "sunscreening" substance of the skin to protect against acute effects of UV-light as well as long-term effects such as development of skin cancer. A1M can be added to existing skin protection agents such as zinc oxide. The application of A1M is single-dose, local and pro-active.

Age-related modification of skin. Several properties of A1M, as described above, suggest that it may promote repair of the extracellular components collagen and ECM, including age-induced oxidative modifications (pigmentation, carbonylation, hydroxylation, cross-linking, etc). The protein may be added to the otherwise healthy skin in several injection sites or as local application on intact skin. The application of A1M can be repeated local single doses.

Atopic dermatitis and psoriasis. A1M may be used to inhibit the oxidative stress associated with the inflammation in skin in these conditions. This includes protection of the cells and repair of cells, collagen and ECM. The application of A1M can be repeated local single doses.

Chronic leg wounds. Chronic wounds, of which most are localized on legs, represent a major health problem and a substantial, increasing burden to health care providers and their financers. A1M is found in chronic leg wounds actively binding to heme, and co-localized to heme mostly around blood vessels. A continuous production of t-A1M in ulcer fluid is also seen. This suggests that A1M is an activated defense mechanism in endogenous wound healing. Excessive haemoglobin, heme and iron, not bound or eliminated by A1M, may be an important component of the chronic inflammation by induction of ROS. Therefore, treatment of the chronic wounds with A1M is proposed to provide an approach for quicker and more efficient ulcer-healing than presently available treatments. The combination of antioxidation-, radical scavenging-, oxidation repair- and "radical sink"-properties of A1M makes the protein a unique and powerful agent for treatment of chronic leg wounds. The application of A1M can consist of several single-doses, should be locally applied in the wound, or even be provided as an intrinsic part of the bandage as a therapeutic agent.

Improved acute wound healing including surgical wound healing. The ECM-promoting properties (molecular and genetic) as well as the anti-inflammatory and repair effects of A1M suggest that the protein may be used in wound healing, for example post-operatively. In addition, it may reduce the negative effects of the blood left from the operation and also prevent infection by binding free iron etc.

F) Oxidative Stress and Reproduction

Through an administration of A1M in a cyclic fashion, either systemically or as vaginal suppositories, dysmenorrea could be treated. Infertility is a common problem that could be an important indication for treatment with A1M. This could be done in a cyclic fashion or as aid in assisted pregnancies, i.e. IVF, embryo transfer, insemination, ICSI etc.

Today, only symptomatic treatment is available for PE, delivery remains the only causal treatment. In accordance with the findings reported herein that free fetal haemoglobin (HbF) is an indicator of PE and that a reduction in the HbF level (or Hb level in general) is likely to reduce any progression of the disease, it is contemplated that any substance that has the ability to i) inhibit formation of free Hb, ii) bind free Hb, and/or iii) reduce the concentration of circulating free Hb would be a potential substance for effective treatment and/or prevention of PE.

Preterm deliveries may be an important indication for A1M use. Again, administration systematically or as vaginal suppositories may be an effective way of stopping the oxidative stress which triggers the premature contractions and ripening of cervix.

G) Oxidative Stress in Neonatal Medicine

All the components of the oxidative stress machinery (FIG. 5), are represented in the pathophysiology of most neonatal complications. A1M could be used in the respirators to protect the immature lungs and in the milk replacement formulas to protect the intestine.

Brain hemorrhages including intraventricular haemorrhage (IVH) are indications for A1M-treatment. Firstly, the anti-haemolytic effects described above (FIG. 9) will lead to a decrease of free haemoglobin-concentrations after bleeding incidents. Secondly, the reduction, scavenger and repair properties of A1M will achieve an immediate scavenging and protecting effect against haemoglobin, heme- and ROS-induced cell and tissue damage. A1M can be injected directly into the ventricles when indications of bleeding are obtained by routine ultrasound scanning of prematurely newborn in the risk-zone.

Hemolytic disease of the fetus/newborn is always mediated via immunoglobulin G (IgG), since IgM molecules do not pass the placenta from the mother to the fetus but only IgG does. This situation is thus similar to the warm autoimmune hemolytic anemias discussed in the previous paragraph. We propose that A1M treatment can be used to help the sensitive fetus cope with the high oxidative stress level caused by the maternal allo-antibodies (often Rh antibodies) destroying the fetal red blood cells and releasing their haemoglobin content. This treatment could be antenatal (by infusion post-cordocentesis) or postnatal as a continuous infusion or together with the blood exchange during which group O RhD neg blood is transfused together with AB RhD neg plasma. The latter could be spiked with high levels of A1M to help bring down the oxidative stress level in these babies.

In Vitro Models to Investigate the Effect of A1M

Placenta Perfusion Model

Today, there are no adequate animal models for PE (preeclamsia). In order to study the effects of free haemoglobin we are using the dual placental perfusion model. The dual-placenta perfusion is a well-established model to study the placental blood flow in-vitro (FIG. 18). Recently, the model was used to mimic PE by inducing ROS formation with xanthine and xanthine oxidase. Our own very recent data indicate that placenta, perfused with xanthine have a gene profile similar to PE placentas indicating that the model is suitable for studying PE in vitro. Furthermore, we have profiled placentas that have been perfused with media containing whole red blood cells. Due to hemolysis of the red blood cells, the level of free haemoglobin increased during perfusion causing oxidative damage, reflected by up-regulation of heme oxygenase and superoxide dismutase gene expression. In a recent experiment, we aimed to mimic the situation seen in PE, by perfusing the fetal circuit with free fetal haemoglobin (2 and 4 µg/ml). Interestingly, the perfusion pressure (blood pressure), increased in a dose dependent manner and haemoglobin gradually leaked into the maternal circulation. We will continue to use the model to study the specific gene and protein expression after perfusion with haemoglobin and evaluate the protective role of A1M (FIG. 17).

In Vivo Models to Investigate the Effect of A1M

We will use a ewe model to mimic PE by infusing free haemoglobin in pregnant ewes. In a pilot study we infused pregnant ewes with free hemoglobin, causing a tendency towards increased blood pressure. We will continue to use the model to study perfusion with haemoglobin and evaluate the protective role of A1M.

The Piglet model will be used for evaluation of IVH-treatment with A1M. The piglet is an ideal animal for study of the human neonatal brain. In both the human and piglet brain, the growth velocity is greatest from a few weeks before birth to a few weeks after birth. The piglet thus replicates the vulnerable state of the human during the brain growth spurt.

EXAMPLES

Antioxidation properties of Alpha-1-microglobulin

The physiological role of A1M is to protect cells and tissues against heme-haemoglobin- and ROS-induced damage (FIG. 4). Below is a description of results supporting this concept.

1. Reduction. A1M has enzymatic reductase and dehydrogenase properties with a wide spectrum of organic and inorganic substrates. The protein reduces heme proteins, free iron and the synthetic compound nitroblue tetrazolium (NBT), using the biological electron donors ascorbate and NADH/NADPH as co-factors (9). The thiol group of Cys34 and the three lysyl residues of K92, K118 and K130 are found in the active site (9). A1M also rapidly reduces the synthetic radical ABTS (10). A1M, added to the culture medium of cells, reduces the cell cytosol and thiol groups on cytosol protein (not shown). A1M also reduces the oxidation products formed on collagen, lipoproteins, and erythrocyte membranes by heme, haemoglobin, hydrogen peroxide and hydroxyl radicals.

Example 1.A

To measure the intracellular oxidation in cells, the redox-sensitive probe $H_2DCFDA$ was added to $0.5$-$1.0 \times 10^6$ K562 cells/ml in serum-free medium to a final concentration of 3 µM. After 30 min, the cells were washed twice in phosphate buffered saline (PBS, 10 mM Na-phosphate pH 7.4, 125 mM NaCl) and suspended in fresh medium. Heme, hydrogen peroxide, ascorbate, A1M or AGP was added as indicated in the figure legends to FIG. 10 and the cells were incubated for various times. After incubation the fluorescence intensity of the suspension was quantified using flow cytometry (BD FACSAria™, BD Biosciences, Palo Alto, Calif., USA). The analysis was performed on 10000 cells using a Coherent® Sapphire™ Solid State Laser (excitation: 488 nm, emission: band pass filter 530/30 nm).

K562 cells were cultured with different concentrations of heme (5-20 µM) for 2 h, and the generation of ROS was evaluated by measuring the amount of oxidized cytosolic $H_2DCFDA$ (FIG. 10A). A slight but significant increase of the relative fluorescence intensity was seen with 5 µM heme, and a clear increase was seen with 10 and 20 µM. The time-dependence of the cytosol oxidation was studied using 10 µM heme (FIG. 10B). The addition of heme induced a rapid increase in the relative fluorescence intensity, which was sustained throughout the incubation period. From the dose and time experiments 10 µM heme for 2 h was chosen for further oxidation experiments. The effects of A1M were examined by adding 2, 5 or 10 µM A1M to the K562 cells, prior to the addition of heme (FIG. 10C). Ten micromolar heme was then added and the cells were incubated for 2 h. A dose-dependent reduction in relative fluorescence by up to approximately 90% was seen when A1M was added. In control experiments, no inhibition of the fluorescence was seen with the lipocalin AGP at the same concentrations as A1M, and 10 µM ascorbate reduced the fluorescence by approximately 50% (FIG. 10C).

The results demonstrate that A1M inhibits cytosol oxidation by heme. We also investigated the repair effect of A1M, i.e. whether A1M could reduce the cytosol in cells that had been preincubated with heme (FIG. 10D). The cells were incubated with 10 µM heme for 30 min and all the unbound heme was washed away. A1M (2, 5 or 10 µM) was added and the cells were incubated for 2 h. The results revealed that A1M was able to significantly reduce cytosol oxidation in a dose-dependent manner. To test whether A1M could reduce the cytosol of "resting", non-stimulated cells, these were incubated with A1M (10 µM) for a period of 2 h (FIG. 10E). Addition of A1M to the cells resulted in a clear reduction in the fluorescence intensity as compared to cells without A1M. Heme, on the other hand, increased the fluorescence as expected. The reduction of unspecific background oxidation seen with A1M was not observed when adding the control protein, AGP.

We investigated whether the anti-oxidative effects of A1M were restricted to cells oxidized with heme, or could also be directed against other oxidants. $H_2O_2$ (50-250 µM)

was used to induce oxidation for a period of 0-20 h (FIG. 11A). $H_2O_2$ induced elevated levels of $H_2DCFDA$ up to a peak at 6 h after which the levels decreased. Simultaneous incubation of cells with A1M (10 or 20 μM) and 50 μM $H_2O_2$ for 6 h showed a dose-dependent reduction in the fluorescence induced by $H_2O_2$, demonstrating the inhibitory effects of A1M (FIG. 11B).

Example 1.B

To measure the reduction potential of A1M on thiol groups, experiments were undertaken with oxidized thiol proteins.

Fluorescent labelling of oxidized thiol proteins was performed by washing and suspending K564 cells in PBS to 0.5-1.0×10⁶ cells/ml and incubated with heme, $NH_4Fe(SO_4)_2$, hydrogen peroxide, ascorbate or A1M as indicated in the figure legends. Reversibly oxidized thiol proteins were then monitored as described in literature. Briefly, protein thiols in their reduced state were blocked by resuspending in a buffer containing 100 mM NEM (N-ethylmaleimide) and incubating at room temperature for 15 min. After lysing the cells, excess NEM was removed by desalting through a Micro Bio-Spin® 6 Chromatography Column (Bio-Rad Laboratories, Hercules, Calif.). The oxidized thiols were then reduced with 1 mM DTT (dithiothreitol) and the resulting free protein thiols were labelled by adding 200 μM 5-IAF. Excess 5-IAF was removed by desalting through a Micro Bio-Spin® 6 Chromatography Column and samples containing 60 μM protein were run on a 10% SDS-PAGE. The gel-electrophoresis was carried out as described by Laemmli [25] in the dark, with a constant voltage of 200 V. After completion of electrophoresis, gels were scanned using a Molecular Imager® FX (Bio-Rad, excitation: 488 nm, emission: 530 nm). Oxidized thiol proteins were quantified by measuring the pixel density of relevant bands, using Adobe Photoshop CS3.

As described above, the anti-oxidative effects of A1M on intra-cellular protein thiol oxidation was measured. Two, five and ten micromolar A1M was added prior to adding 10 μM heme to K562 cells and these were then incubated for 6 h. Intracellular proteins labelled with the disulfide-specific fluorescent probe 5-IAF were separated by SDS-PAGE. The oxidized thiols were visualized by fluorimetry (FIGS. 11C and 11D) and the strongest bands quantified by measuring pixel density (FIGS. 11E and 11F).

Heme induced an increased protein thiol oxidation (FIG. 11C,E) and the thiol label intensity of the four strongest bands (migrating as 50, 55, 60 and 66 kDa; marked by arrows) was inhibited by A1M in a dose-dependent manner down to the level of resting cells. Hence A1M show strong reducing properties on oxidized thiol groups. The weakly stained bands showed less upregulation by heme and less inhibition by A1M (not shown), perhaps because of non-specific binding of the probe. Furthermore, A1M also inhibited non-heme induced protein thiols: a mixture of $Fe^{3+}$, ascorbate and hydrogen peroxide (10 μM, 100 μM and 20 μM, respectively) was used to generate hydroxyl radicals by the Fenton-reaction. The mixture resulted in an increased level of oxidized protein thiols (FIG. 11D,F) and the thiol label intensity of the five strongest bands (migrating as 50, 60, 66, 80 and 120 kDa; marked by arrows) decreased by addition of A1M.

2. Radical scavenging. A1M can react with small organic radicals by using a combination of enzymatic reductase activity (see above) and covalent binding to amino acid side-chains ("trapping"). Heme, kynurenin and the tyrosyl-radical are physiological examples of radicals scavenged by A1M (6-8, 10). Thus, the A1M-chromophores can be heme- and kynurenin degradation products, and perhaps also other similar products. The heme-binding and degradation is much enhanced by proteolytic cleavage of A1M, a reaction which is induced by haemoglobin and results in elimination of the four C-terminal aminoacids of A1M, Leucine-Isoleucine-Proline-Arginine (7). The shorter (truncated) form, which thus has enhanced heme-degrading properties, is called t-A1M. Antioxidation by heme-scavenging is probably not restricted to haemoglobin. A reaction between MPO and A1M results in formation of t-A1M and transfer of the heme-group from MPO to A1M (not shown). Therefore, A1M may function as an inhibitor of the damaging effects of the oxidative burst of neutrophil granulocytes (see above) on by-stander tissue components.

Example 2.A

ABTS assay: The reductase activity of A1M was analyzed by reaction with the 2,2'-azinobis-(3-ethylbenzothiazoline-6-sulfonic acid)-radical (ABTS-radical) as described previously. Briefly, ABTS-radical was prepared by oxidation of 7 mM ABTS with 2.45 mM potassium disulfite in water for at least 5 h in the dark, and using the resulting ABTS-radical solution within 24 h. Heme (50 μM) was incubated with 0.5-1.0×10⁶ K562 cells, the cells were washed and then incubated 2 h with 10 μM A1M as indicated in the figure legends. Supernatant aliquots (>5 μl) were then added to a 35 μM solution of ABTS-radical in 25 mM Na-phosphate, pH 8, giving a final concentration of 3 μM A1M. The absorbance of the ABTS-radical was read every 10 s at 735 nm, for a total of 3 min (FIG. 12B). The rate of reduction of the ABTS-radical was estimated by linear regression of the first five points, i.e. 40 s of the reaction, including time-point zero.

Absorbance scanning of solubilized K562 cells was performed by washing and suspending the cells in PBS to 0.5-1.0×10⁶ cells/ml and incubated with heme or proteins in various steps as indicated in the figure legends. After incubation, the medium was saved and the cells were washed and solubilized with buffer containing 50 mM Tris-HCl, pH 8.0; 2 mM EDTA; 1% NP-40; 1 μg/μl pepstatin; 5 μg/μl antipain; 10 μg/μl leupeptin. Both solubilized cells and medium were then analyzed visually and spectrophotometrically by reading the absorbance spectra (300-700 nm).

Gel chromatography: K562 cells were washed, and incubated (0.5-1.0×10⁶ cells/ml) with buffer or 50 μM heme, then washed and incubated 2 h with buffer or 10 μM A1M as indicated in the figure legends. After incubation, cells and culture medium were separated by centrifugation and culture medium was analyzed by gel-chromatography as discussed in subsequent paragraphs below. This was performed on a 25 ml-Superose 12 HR 10/30 column (GE Healthcare) using a Fast Performance Liquid Chromatography (FPLC) apparatus (Bio-Rad) equipped with a 0.5 ml sample injection loop, monitoring the eluate at 280 and 405 nm and collecting 0.5 ml fractions. The column was equilibrated and eluted with 20 mM Tris-HCl, pH 8.5; 0.1 M NaCl; 0.02% $NaN_3$.

It was shown recently that A1M can reduce the ABTS-radical, a stable organic radical, in a semi-catalytic manner, leading to formation of free, reduced ABTS and covalent attachment to side-groups on the protein [10]. We investigated this property of the protein after incubation with cells and/or heme. The disappearance of the ABTS-radical (abs 735 nm) was seen with A1M alone, or A1M incubated with heme or heme plus cells (FIG. 12B). The reduction (reaction) rate was slightly, but significantly increased when A1M was incubated with heme-loaded cells or with 10 µM heme (P<0.05) (FIG. 12C). Background activity, i.e. a very slow disappearance of the ABTS-radical, was seen with the controls.

Most of the heme (abs 405 nm) was co-eluted with the protein (abs 280 nm), suggesting that it is bound to A1M. Furthermore, increased amounts of dimeric and higher-order aggregates of A1M were seen after heme-binding, as compared to A1M incubated with cells but without heme (FIG. 12A).

To study the radical scavenging mechanism, the reaction between A1M and the synthetic, model free radical ABTS was characterized in detail. It was shown that A1M reduced 5-6 molecules of the ABTS-radical in a rapid semi-catalytic reaction, and covalently trapped 3 additional ABTS-radicals by binding on tyrosyl side-chains in a modified, oxidized form giving the protein a purple colour (10). Two of the modified Tyr-residues were identified (Y22, Y132) and localized on the A1M-molecule by mass-spectrometry (FIG. 6).

It is important in this context that A1M, after binding a maximum load of radicals does not present any oxidative stress to tissue components, i.e. both the radicals and the A1M-protein itself are electroneutral. In other words, ROS, radicals and other oxidants are completely eliminated by A1M, hence the metaphor "radical sink".

Example 2.B

Heme scavenging mechanisms of A1M were further studied by analyzing the interactions between the protein and cell-bound heme. Cells were incubated with 10 µM heme for 30 min, excess heme washed off and A1M or the control protein AGP added to a concentration of 2 or 10 µM and incubated for 2 h. The culture media were saved, cells washed and solubilized, and both media and solubilized cells analyzed by spectrophotometry (FIG. 7A) and visually (FIG. 7B). Heme incorporated to the cells was seen as a strong brown-colouring of the cells; the typical absorbance spectrum with a non-distinct peak was detected around 400 nm. When adding A1M, the heme was almost completely removed from the cells and instead found in the medium. The control protein AGP at the same molar concentrations had much less effect on the cell-bound heme (FIG. 7B).

3. Inhibition of Oxidative Damage to Biological Tissue

Example 3.A

A1M was also shown to inhibit the propagation of cell-death induced by charged particle irradiation of HepG2 cell monolayers. The cells were irradiated with a low dose of alpha-particles at an area of approximately 50 µm². The directly hit cells were killed and the cells peripheral to the irradiation area, not directly hit by the particles (=bystander cells), showed a delayed and slowly accumulating necrosis up to 5 days after the irradiation. Furthermore, a significant increase in apoptosis, protein carbonyl groups, and expression of the stress response genes heme oxygenase-1, was observed in the whole cell population (FIG. 8 A-C). Addition of A1M reduced the amount of dead cells by approximately 50% in irradiated cells and 100% in bystander cells, and completely inhibited the irradiation-induced apoptosis, formation of carbonyl groups and upregulation of heme oxygenase-1, (FIG. 8 A-C). Irradiation induced an upregulation of endogenous synthesis and secretion of A1M and an increased uptake of A1M from the medium. A possible mechanism for the bystander cell killing is by oxidant- and ROS-production, and a possible mechanism for the inhibition by A1M is by antioxidation and radical-scavenging.

Example 3.B

A1M inhibited the oxidation of low density lipoprotein (LDL) by heme, hydrogen peroxide and hydroxyl radicals, the oxidation of erythrocyte membranes by hydroxyl radicals, and the oxidation of collagen monomers by heme and hydrogen peroxide (not shown). Oxidative modification of collagen and low-density lipoproteins (LDL) is involved in the pathogenesis of arthritis, diabetes and cardiovascular diseases. Collagen is especially sensitive to oxidative stress because the molecules have a very slow turnover-rate, i.e. the fibrils can last a life-time. Therefore, oxidation of collagen is involved in the pathogenesis of arthritis, diabetes and cardiovascular diseases. Collagen is also a major constituent of the basement membranes of blood vessels, glomerular filtration barrier and blood-brain barrier and oxidative damage to collagen therefore affects the function of these barriers (see below).

To investigate the cell protective properties of A1M to exogenous oxidative stress, in human cell lines, the erythroid cell line K562 was incubated in serum free growth medium and exposed to exogenous oxidative stress by culturing the cells with different concentrations of heme (5-20 µM) (FIG. 10 A, B). As shown in FIG. 10 C, addition of A1M to the growth medium exhibits an inverse dose-dependent antoxidation effect where the oxidative stress diminishes with increasing amounts of A1M. The results demonstrate that A1M is able to not only inhibit oxidative stress during its formation, but also (as shown in FIG. 10 D) remove the oxidative stress after incubation of the cells under oxidative stress in heme-containing medium.

To illustrate the severity on cell viability, the effect of heme and A1M was tested by adding 20-500 µM heme to K562 cells for 4 hours and subsequently testing the viability by staining with PI (propidium iodide) and FACS-analysis. To assay the viability of the K562 cells, the cells were washed and suspended in PBS to $0.5$-$1.0 \times 10^6$ cells/ml and incubated with heme, human A1M and/or AGP as indicated in the figure legends. After incubation the nucleus-staining dye PI was added to a final concentration of 10 µM and the fluorescence intensity of the suspension was quantified using flow cytometry (BD FACSAria™, BD Biosciences, Palo Alto, Calif., USA). The analysis was performed on 10000 cells using a Coherent® Sapphire™ Solid State Laser (PE-channel, filter-setting 556 LP and 576/26 BP).

A clear dose-dependence of the cell death was observed (FIG. 13B) up to almost 100% at 500 µM heme. No effect was seen using corresponding amounts of the heme solvent, DMSO (not shown). The ability of A1M to rescue cells from death was examined by adding A1M (2, 5 or 10 µM) or AGP (10 µM) to the cells, prior to the addition of 200 µM heme and incubating for 4 h. Approximately 70% of the dead cells could be rescued with the addition of A1M at the highest concentrations (FIG. 13C). No significant effect was observed with AGP.

Example 3.C

To test the role of intracellular A1M, three siRNA-targeting A1M nucleotides were purchased from Sigma-Aldrich and evaluated for their ability to inhibit/silence A1M expression in human K562 cells. The best results, evaluated by real time PCR analysis of the A1M/glyceraldehyde-3- phosphate dehydrogenase (G3DPH) mRNA ratio (see below), were obtained with the A1M siRNA pair (NM_001633/1): 5'-CCUAUGUGGUCCACACCAA-3' and 5'-UUGGUGUGGACCACAUAGG-3'. This siRNA species was subsequently used for all experiments. The transfection of siRNA was conducted according to the protocol from OZ Biosciences (Marseille, France). Briefly, siRNA was diluted in culture medium, containing Lullaby®-siRNA transfection reagent (OZ Biosciences), to a final concentration of 5 nM. This solution was incubated for 20 min in room temperature and added to a pellet of $2 \times 10^6$ cells drop by drop. The cells were then cultivated under standard conditions. After 24 h, the cells were washed, loaded with $H_2DCFDA$, oxidized with heme and analyzed with flow cytometry as described above. Alternatively, cells were resuspended in serum free medium with or without heme, according to the figure legends, and analyzed with real time PCR.

The A1M gene was silenced by adding A1M-specific siRNA and the cells challenged with 20 µM heme. The A1M mRNA was partially silenced (FIG. 13E, left panel), resulting in a significant increase of cytosol oxidants as measured by the $H_2DCFDA$ probe (FIG. 13E, right panel). Moreover, A1M added to the culture medium inhibited cytosol oxidation and heme oxygenase-1 expression by heme, hydrogen peroxide and hydroxyl radicals (not shown).

Example 3.D

Fluorescence microscopy of the K562 cells were washed and suspended in PBS to $0.5-1.0 \times 10^6$ cells/ml and incubated with human A1M as indicated in the figure legends. The cells were washed, placed on ice and resuspended in blocking solution (5.4 mM KCl; 1.2 mM $KH_2PO_4$; 0.8 mM $MgSO_4$; 5.6 mM D-glucose; 127 mM NaCl; 10 mM Hepes; 1.8 mM $CaCl_2$; pH 7.3; 1% BSA; 5% goat serum) for 15 min. First, cell surface staining was carried out by incubating for 15 min on ice with mouse monoclonal antibodies against A1M (5 µg/ml). This was followed by washing and incubating for 15 min on ice with goat anti-mouse IgG Flab')$_2$ fragments (Alexa Fluor® 594; Invitrogen, Eugene, Oreg., USA). After washing, total staining of the cells (cell surface+cytosol) was performed by suspending in ice-cold Na-medium, fixation with 1% BD CellFIX (BD Biosciences, Belgium) on ice for 15 min and at room temperature for 45 min, followed by permeabilization in 0.02% Triton-X and blocking in 1% BSA, 5% goat serum, 0.2% Tween-20. The cells were then stained at 4° C. overnight with mouse monoclonal antibodies against A1M at 5 µg/ml. Subsequently, goat anti-mouse IgG F(ab')$_2$ fragments (Alexa Fluor® 488; Invitrogen, Eugene, Oreg., USA), was applied for 1 h at room temperature. Cells were mounted using ProLong Gold AntiFade Reagent with DAPI (Invitrogen). Visual inspection and recording of images was performed using a Nikon Eclipse TE300 inverted fluorescence microscope equipped with a Hamamatsu C4742-95 cooled CCD camera, using a Plan Apochromat 100× objective.

Since endogenously produced A1M is secreted from the cells, both this and exogeneously added A1M is found in the cell-medium, outside the cells. As described above, by using fluorescence microscopy, we investigated the cellular localization of A1M. Most of the endogenous protein was detected as a patchy staining on the surface of the cells, as shown by incubation with anti-A1M before and after permeabilization and fixation. Weak staining of intra-cellular compartments was also observed after permeabilization. Approximately 60% of the cells were positive for A1M staining. However, a much stronger staining was obtained after cells had been incubated with exogenous A1M, and also in this case most of the staining was located at the cell surface (approximately 90% of the cells) in a patchy pattern, as shown by incubation with anti-A1M before and after permeabilization and fixation.

Statistical analysis of the results from triplicate experiments are presented as mean±SD. Statistical analysis was performed in the computer program Origin (Microcal Software, Inc., Version 6), comparing groups with Student's t test.

4. Inhibition of Cell Lysis and Cell Repair

Example 4.A

Cell death of irradiated HepG2 cells was inhibited by A1M, as described above (exemplified in FIG. 8A). A1M also inhibited heme-induced lysis of K562 cells. For example, 200 µM heme killed 50% of the cells but adding 2 µM A1M lowered the number of dead cells to 15%, i.e. by approximately 70% (exemplified in FIG. 13 B,C). A1M can also inhibit lysis of red blood cells by ROS (hydrogen peroxide and hydroxyl radicals). This is exemplified in FIG. 9A. Hydroxyl radicals, generated by the Fenton reaction, induced lysis of red blood cells and the lysis could be inhibited by A1M.

5. Repair of Oxidative Modification

As mentioned above, A1M can reduce oxidative modifications on cells and molecules after their formation and removal (washing) of the oxidation agents. This may be a result of reduction, radical scavenging or both. For example, free heme, which is a hydrophobic molecule that can pass through cell membranes, is absorbed by cells and is found mostly in the cytosol (FIG. 7C,D) where it induces oxidation. Adding A1M to heme-loaded cells effectively removes the heme (FIG. 7C-D) and the cytosol oxidation (FIG. 7A).

Example 5.A

As another example of such reparation, A1M reversed the inhibition of collagen fibril formation (measured by EM) induced by heme and ROS (FIG. 14). A1M binds to collagen (not shown) and our results shows that it is probably involved in physiological protection of the fibrils against oxidation. These results also suggest that A1M may be used in therapeutic applications to restore, or repair tissues damaged by haemoglobin- or ROS-induced oxidation.

6. Up-regulation of Gene Expression In Vitro and In Vivo

Example 6.A

To investigate the transcriptional regulation of A1M, Real-Time PCR was applied. For Real-Time PCR, total RNA was isolated from K562 cells using the acid guanidinium phenol chloroform method supplied by QIAGEN Sciences (Maryland, USA). The OD ratio (optical density at 260 nm/280 nm) of RNA was always greater than 1.8. Reverse transcription was performed on 3 µg total RNA at 42° C. for 60 min in the presence of 0.5 µg oligo(dT)$_{18}$ primer, 200 U reverse transcriptase and 20 U RiboLock™ Ribonuclease inhibitor in reaction buffer (RevertAid™ H Minus First Strand cDNA Synthesis Kit, Fermentas GMBH, St. Leon-Rot, Germany). Real-time PCR was used to examine the expression of the A1M and heme oxygenase-1 (HO-1) mRNA in K562 cells exposed to heme, hydrogen peroxide or a mixture of $(NH_4)Fe(SO_4)_2$, hydrogen peroxide and ascorbate. Human G3DPH was used to normalize the expression of A1M and HO-1 which are depicted in the figure as ΔΔCt. Primers were designed accordingly: A1M forward primer 5'-CACTCGTTGGCGGAAAGG-3', reverse primer 5'-ACTCATCATAGTTGGTGTGGAC-3'; HO-1 forward primer 5'-CAACAAAGTGCAAGATTCTG-3', reverse primer 5'AAAGCC-CTACAGCAACTG-3'; G3DPH forward primer 5'-TGGTATCGTGGAAGGACTC-3', reverse primer 5'-AGTAGAGGCAGGGATGATG-3'. The expression was analyzed using iQ SYBR Green Supermix (Bio-Rad). Amplification was performed at 55° C. for 40 cycles in iCycler Thermal Cycler (Bio-Rad) and data analyzed using iCycler iQ Optical System Software.

The heme oxygenase 1 (HO-1)-gene is up-regulated in K562 cells as a result of heme exposure. We analyzed the effect of A1M on oxidant-induced HO-1 expression (FIG. 13A). As expected, HO-1 was up-regulated by 10 μM heme, 50 μM H2O2 or a mixture of 10 μM Fe3+, 20 μM H2O2 and 100 μM ascorbate, and the up-regulation was reversed by 10 μM A1M. The expression of the house-keeping gene G3DPH was not affected by any of the additions.

It was shown previously that small amounts of A1M are secreted from K562 cells, and that the secretion was increased after incubation with haemoglobin or ROS. FIG. 13D shows real time PCR-analysis of A1M-mRNA in K562 cells incubated with medium, 10 μM heme, 50 μM $H_2O_2$ or a mixture of 10 μM $Fe^{3+}$, 20 μM $H_2O_2$ and 100 μM ascorbate. All these oxidants induced an increase in the A1M mRNA levels.

The expression of A1M is increased by exposure of cells to haemoglobin, heme and ROS in hepatocyte-, histiocyte- and erythrocyte cell lines. An upregulation of A1M is also seen in keratinocytes and fibroblasts in response to haemoglobin and ROS (not shown). This may be important for the antioxidation defense in the skin where keratinocytes constitute the major cell type. Furthermore, endogenously produced A1M is localized on the surface of K562 cells, probably after secretion and uptake by cell surface receptors (not shown), and exogeneously added A1M is also found mainly on the cell surface (not shown). Thus, peripheral cells may be protected both by plasma A1M produced by the liver and locally synthesized A1M.

Example 6.B

New results show a correlation between the concentrations of A1M and haemoglobin, and between A1M and protein carbonyl groups, respectively, in the human disease (PE). PE is a disease of pregnancy with the clinical symptoms high blood pressure and proteinuria. It is known that PE is a disease with a certain degree of oxidative stress. Our results show that the concentrations of plasma haemoglobin concentrations and plasma protein carbonyl group, a biomarker of oxidative stress are correlated to the disease (not shown). We also found that the concentrations of A1M in plasma and placenta tissue extracts were significantly elevated in PE-patients and correlated to plasma haemoglobin and protein carbonyl group concentrations (FIGS. 15 and 16A-D). These results indicate that the synthesis of A1M are upregulated in vivo in diseases with oxidative stress and elevated concentrations of haemoglobin.

7. Stimulation of Extracellular Matrix Growth

As described above A1M has protective and repair effects on collagen during oxidative stress. Collagen is a major molecular component of extracellular matrix (ECM) in for example basal membranes and skin tissue. New experimental results also indicate that A1M have positive effects on ECM growth (Table 3). Human placentas were perfused in vitro with A1M or with buffer only and the tissue then sampled for investigation of mRNA-levels using gene array technique (Table 3) and ultrastructure using electron microscopy (FIG. 14). As shown in the Table 3, many extracellular matrix gene groups were upregulated by A1M perfusion. Electron microscopy showed a clear difference in collagen structure in the two groups. Perfusion with buffer resulted in breakdown of collagen bundles, thinner fibrils and an abundance of scattered monomers, whereas perfusion with A1M gave the opposite result—an increase in the thickness and number of fibrils (FIG. 14). It is therefore contemplated, that A1M may be applied locally by a formulation in which A1M is included in a patch, impregnated into bandages or included in lotions.

TABLE 3

Gene groups with increased expression levels in perfusion with A1M compared to medium only.

| Category | Name of group | Count | P-value | Fold change |
|---|---|---|---|---|
| GO:0005581 | Collagen | 4 | 0.00035 | 28.49 |
| GO:0044421 | Extracellular region part | 10 | 0.00124 | 3.65 |
| GO:0006817 | Phosphate transport | 4 | 0.00416 | 12.10 |
| GO:0006820 | Anion transport | 5 | 0.00479 | 7.18 |
| GO:0005201 | ECM structural constituent | 4 | 0.00504 | 11.33 |
| GO:0005578 | Proteinaceous ECM | 6 | 0.00526 | 5.22 |
| GO:0031012 | ECM | 6 | 0.00566 | 5.13 |
| GO:0044420 | ECM part | 4 | 0.00619 | 10.50 |
| GO:0005576 | Extracellular region | 11 | 0.01127 | 2.438 |
| GO:0003886 | DNA (cytosine-5)-methyltransferase activity | 2 | 0.01290 | 151.5 |
| GO:0005496 | steroid binding | 3 | 0.01568 | 15.41 |
| GO:0009008 | DNA-methyltransferase activity | 2 | 0.01610 | 121.1 |
| GO:0015698 | Inorganic anion transport | 4 | 0.01836 | 7.02 |
| GO:0005887 | Integral to plasma membrane | 10 | 0.01890 | 2.401 |
| GO:0031226 | Intrinsic to plasma membrane | 10 | 0.02038 | 2.371 |
| GO:0005615 | Extracellular space | 6 | 0.02749 | 3.45 |
| GO:0006807 | Nitrogen compound metabolic process | 6 | 0.02770 | 3.44 |
| GO:0007423 | Sensory organ development | 3 | 0.04335 | 8.89 |
| GO:0006783 | Heme biosynthetic process | 2 | 0.04726 | 40.6 |

Placenta perfusions, extractions and measurements were carried out on term placenta tissues from healthy individuals as described (Centlow M, Junus K, Nyström H, May K, Larsson I, Olsson MG, Åkerström B, Sager R, Schneider H, Hansson SR. Perfusion of the human placenta with red blood cells mimics preeclampsia in vitro. Z Geburtshilfe and Neonatologie, in press) with 10 μM A1M in tissue culture medium NCTC-135, diluted with Earle's buffer containing 40 g/l bovine serum albumin, 10 g/l dextran 40, 1.33 g/l glucose, 2500 IU/l heparin and 250 mg/l clamoxyl, or medium only. A1M was prepared as described (Kwasek A, Osmark P, Allhorn M, Lindqvist A, Akerstrom B, Wasylewski Z. Production of recombinant human A1M and mutant forms involved in chromophore formation. Protein Expr Purif 2007; 53(1): 145-52.). The values compare placenta tissue extracts after the perfusion. Count: total number of A1M-and control perfusions analyzed, p-value: significance of the difference, fold change: values of A1M-perfusions divided by values of control-perfusions.

Example 7.A

To investigate the potential for use of microglobulins in general and A1M in particular, for the treatment of inflammatory dermatological diseases, a skin penetration experiment was undertaken. The dermatological diseases of interest are inflammatory diseases involving impaired barrier function such as atopic dermatitis and psoriasis. The model used takes into consideration the impaired barrier function and is described in the literature, U. Jacobi and K. Engel, et. al. in "Penetration of Pollen Proteins into the Skin" Skin Pharmacol Physiol 2007; 20:297-, as a relevant model for determination of protein delivery through skin in atopic dermatitis patients.

A bronaugh cell diffusion unit is used. The equipment consists of 14 cells and each cell has lower part where the receptor medium, 20 mM TRIS, 0.1 N NaCl at pH 8, is pumped through at a rate of 1.4 ml/hour and an upper part where the product, in this case a 3 w/w % solution of A1M, is administered. The upper and lower parts are separated by a pig ear skin membrane.

The membranes used are skin from the inner ear of domestic pig. The reason is a long experience giving rise to small variations in penetration behavior and the fact that porcine A1M is separable from human ditto by radio immuno assay, RIA. The membranes are tape stripped 25 or 50 times respectively prior to the penetration experiment.

For cells having membranes that are tape stripped 25 times the penetration data is demonstrated in tablet while in table 2 the penetration data of membranes that has been tape stripped 50 times. The experiment was terminated after 24 hours. The amount absorbed, the amount passing through skin and tissue concentration, what is found in the tissue, is listed in table 2 and 3.

TABLE 2

| Cell number | 1 | 2 | 3 | 4 | 5 | 6 | 7 | Average |
|---|---|---|---|---|---|---|---|---|
| % absorbed | 1.658 | 0.863 | 1.015 | 0.136 | 0.217 | 0.131 | 0.431 | |
| Membrane thickness (mm) | 0.851 | 0.734 | 0.658 | 0.955 | 0.896 | 0.727 | 0.514 | |
| Membrane volume mL | 0.054 | 0.046 | 0.041 | 0.060 | 0.056 | 0.046 | 0.032 | |
| Amount absorbed (μg) | 3.015 | 1.568 | 1.846 | 0.246 | 0.395 | 0.238 | 0.783 | |
| Tissue conc (μg/ml) | 56.23 | 33.91 | 44.52 | 4.10 | 7.00 | 5.21 | 24.17 | 25.02 |

TABLE 3

| Cell number | 8 | 9 | 10 | 11 | 12 | 13 | 14 | Average |
|---|---|---|---|---|---|---|---|---|
| % absorbed | 0.45 | 1.20 | 0.76 | 0.84 | 0.86 | 0.47 | 0.19 | |
| Membrane thickness (mm) | 0.851 | 0.734 | 0.658 | 0.955 | 0.896 | 0.727 | 0.514 | |
| Membrane volume mL | 0.054 | 0.046 | 0.041 | 0.060 | 0.056 | 0.046 | 0.032 | |
| Amount absorbed (μg) | 0.823 | 2.173 | 1.377 | 1.536 | 1.556 | 0.847 | 0.337 | |
| Tissue conc (μg/ml) | 15.35 | 46.99 | 33.23 | 25.53 | 27.57 | 18.50 | 10.40 | 25.37 |

Although the variation is large, which is normal in this type of single administration experiments, the results indicates that a tissue concentration of about 25 μg/ml, or 1 μM is generated after a single administration. This concentration has previously been shown to have a biological effect and is comparable to the concentration in human blood plasma. Further administration of A1M will generated higher tissue concentrations. It can therefore be concluded that A1M will be delivered to the tissue and the effect can be utilised in the treatment of inflammatory skin diseases involving an impaired barrier function.

Examples of Pharmaceutical Compositions Comprising A1M

Examples below are solely included for inspiration and may not be considered limiting in any matter. Formulations may be combined, adjusted and applied by the user in any way that supports the optimal treatment and patient compliance.

Examples include formulations for topical or mucosal application, formulations for parenteral application and examples for alternative routes of administration.

Example 1

Topical Composition

Compositions comprising the following ingredients will be made

| Ingredient | Function | Concentration range |
|---|---|---|
| A1M | Drug substance | 10-40% w/w |
| | Penetration enhancer(s) | 0-10% w/w |
| | Solubilizer(s) | 2.5-20% w/w |
| | Ointment base, Suspension base or Emulsion base | 30-87.5% w/w |

Example 2

Parenteral Composition

Compositions comprising the following ingredients will be made

| Ingredient | Function | Concentration range |
|---|---|---|
| A1M | Drug substance | 5-40% w/w |
| | Solubilizer(s) | 0-10% w/w |
| | Solvent(s) | up to 100% w/w |

Example 3

Ointment, Hydrophilic Petrolatum

| Ingredient | Amount |
|---|---|
| A1M | 5-30% w/w, notably 10-20% w/w |
| Cholesterol | 2-10% w/w, notably 3% w/w |
| Stearyl alcohol | 2-10% w/w, notably 3% w/w |
| White wax | 5-15% w/w, notably 8% w/w |
| White petroleum | 70-90% w/w, notably 86% w/w |

Example 4

Hydrophilic Ointment

| Ingredient | Amount |
|---|---|
| A1M | 5-30% w/w, notably 10-20% w/w |
| Methylparaben | 0.01-0.05% w/w, notably 0.025% w/w |

-continued

| Ingredient | Amount |
| --- | --- |
| Propylbaraben | 0.005-0.03% w/w, notably 0.015% w/w |
| Sodium Lauryl Sulfate | 0.5-5% w/w, notably 1% w/w |
| Propylene glycol | 5-20% w/w, notably 12% w/w |
| Stearyl alcohol | 10-50% w/w, notably 25% w/w |
| White petroleum | 10-50% w/w, notably 25% w/w |
| Purified water | 25-75% w/w, notably 37% w/w |

Example 5

Liquid for parenteral administration (e.g. Intramuscular-, intravenous-, subcutaneous- or intradermal administration). Concentration ranges are recommendations and may exceeded if relevant.

| Function | Example | Normal amount |
| --- | --- | --- |
| Active drug | A1M | 1-50% |
| Solvent | e.g. Ethanol, Glycerol, Propylenglgycol or Macrogol 400 | 0-30% |
| Solubilizer | e.g. Polysorbat 80 | 0-5% |
| Emulsifier | e.g. Lecithin | 0-2% |
| Isotoni giving compounds | e.g. NaCl or Glucose | 0-0.9% |
| Complex-former | e.g. Sodiomedetat | 0-0.1% |
| pH adjustment | e.g. HCl or NaOH | — |
| Buffer | e.g. Citrate-, Acetate- or Phosphate buffer | 0-5% |
| Preservatives | e.g. Phenol, Chlorcresol, Parabene(s), Benzylalcohol or Thiomersal | 0-2% |
| Viscosity adjustment | e.g. Methyl cellulose, Sodiumcarboxymethylcellulose, Glycerol or Macrogol | 0-1% |

LEGENDS TO FIGURES

FIG. 1. Human health is dependent on a balance between oxidants and antioxidants. Oxidants are produced continuously within the organism as a result of normal metabolism and are introduced from outside via food, air, etc. Antioxidants are produced by the body and, less importantly, via food. Imbalance between oxidants and antioxidants can be caused by increased production or intake of exogeneous oxidants or decreased production of endogenous antioxidants. This result in oxidative stress and various diseases as described in the text.

FIG. 2. A. Major antioxidation mechanisms. 1. Catalytic reduction of oxidant using electrons derived from cellular metabolism or other sources. 2. Non-catalytic reduction of oxidants using electrons derived from the antioxidant itself, but re-generating the antioxidant with electrons derived from cellular metabolism or other sources. 3. Scavenging of oxidant by covalent binding to the antioxidant. When the scavenging reaction is oxidative, electrons are derived from cellular metabolism or other sources. Large circle: antioxidant; small amoeba: deleterious oxidant (radical); small circle: de-toxified oxidant (radical). B. Antioxidation mechanisms of A1M. 1. Catalytic reduction of oxidant using electrons derived from cellular metabolism or other sources. 2. Non-catalytic reduction of oxidants using electrons derived from the A1M itself. 3. Scavenging of oxidant by covalent binding to the antioxidant. The scavenging reaction is reductive, i.e. electrons are produced by the reaction. 4. Repair of oxidative modifications.

Large circle: A1M; small amoeba: deleterious oxidant (radical) or oxidative modification of cell or molecule; small circle: de-toxified oxidant (radical) or reduced modification of cell or molecule.

FIG. 3. Model of the structure of A1M. The model was prepared as described (ref 29). The eight β-strands, shown as ribbons, form a slightly cone-shaped cylinder with a hydrophobic interior: the "lipocalin pocket". One side of the lipocalin pocket is open (shown by the arrow), i.e. it permits entrance of small molecules. The opposite side is closed. Two α-helices are shown as cylinders. The positions of three carbohydrate groups (T5; N17; N96) and four side-chains involved in reductase activity (C34; K92; K118; K130) are shown.

FIG. 4. Antioxidant properties of A1M. Oxidants, exemplified by heme and hemoglobin, induce formation of free radicals and reactive oxygen species (ROS). These cause oxidative damage by harmful oxidation reactions with tissue components. A1M interferes with this process=Antioxidation. Haemoglobin and oxidants stimulate the synthesis of A1M. Oxidative damage is involved in disease development, exemplified by preeclampsia. A1M is involved in the diseases by antioxidation and its synthesis is stimulated by oxidants during the disease. Red lines: inhibitions; blue arrows: positive effects.

FIG. 5. The oxidative stress machinery shown as a red wheel, turned by different gears, blood metabolites (in red), ischemia (green), inflammation (yellow) and environmental factors (blue).

FIG. 6. Tentative mechanism of the reactions between A1M and ABTS-radical. The figure illustrates schematically the electron-flow, reaction-mechanism and structural relationship between reactive amino acid side-chains of the radical-scavenging mechanism of A1M. A1M is represented by a "lipocalin" barrel (see FIG. 2) with Y132 and the thiolate group of C34 high-lighted. The latter is located on a large, flexible loop. The C34 thiolate group reacts with ABTS-radical, and a thiolyl radical and reduced ABTS are formed. The thiolate is then regenerated by intramolecular reaction with Y132, producing a tyrosyl radical. Subsequently, the tyrosyl radical reacts with another ABTS-radical, forming a stable purple tyr-ABTS adduct. The same reaction is also proposed for Y22, and an additional tyrosine with an unknown location.

FIG. 7. A1M cleans K562 cells from deposited heme. A: K562 cells were cultured with buffer or 10 μM heme for 30 minutes, washed, and incubated with A1M for 2 hours, washed and solubilized by suspending in 1% NP-40. The culture medium and cell suspension were then analyzed by reading the absorbance spectra. B: Cells were incubated with buffer or 10 μM heme for 30 min (Step 1), washed and then incubated with buffer, 10 μM A1M or 10 μM AGP for 2 hours (Step 2). Supernatants and cells, solubilized in 1% NP-40, were photographed separately.

FIG. 8. Inhibition of irradiation-induced cell death. A: Human hepatoma (HepG2) cells were grown to confluency and irradiated with 1.3 Gy alpha-particles and then cultured for 3 days. The irradiation area was 50 μm. The cell death at the irradiation spot ("irradiated cells") or 0.5 cm from the irradiation spot ("bystander cells") was measured by uptake of propidium iodide, using fluorescence microscopy at various time-points after the irradiation. Irradiation was performed on cells cultured in medium (●), on cells cultured in medium+5 μM A1M (▲). Control cells (■) cultured in medium were not irradiated. B and C: Human hepatoma (HepG2) cells were grown to confluency and irradiated with 0.2 Gy alpha-particles. Fresh medium with 0 or 10 μM A1M was added and the cells incubated for 0-72 hours. At the end-point of all incubations cells were harvested and the protein carbonyl group concentrations (B) and HO-1 mRNA levels (C) were analyzed by ELISA and real-time PCR, respectively. All steps, except the irradiation, were performed with identical control cultures. Cultures incubated with 10 µM A1M (▼) or medium only (○) and non-irradiated cultures with 10 µM A1M (Δ) were investigated. Non-irradiated cell cultures were set to zero. HO-1 threshold cycle values were normalized against G3DPH and ΔΔCt was calculated by normalizing against non-irradiated cell cultures. Results from triplicate experiments are presented as mean±SD. Statistical comparison between groups was made using Student's t test. *P<0.05; ***P<0.001.

FIG. 9. Antihemolytic effects of A1M. Red blood cells were prepared by density gradient centrifugation, washed with PBS and suspended to 1% in PBS. A and B: Aliquots were incubated 20 h at 37° C. with buffer (control), 50 µM Fe3+, 20 µM $H_2O_2$ and 250 µM ascorbate (Fenton-reaction reagents), Fenton-reaction reagents+2 µM A1M, or Fenton-reaction reagents+10 µM A1M. After centrifugation, the light absorbance of the supernatant was read by scanning spectrophotometry (A) and the LDH concentration determined by a colorimetric assay (B). C: Cells were incubated for 5 min, 1 h and 20 h at 37° C. with buffer ("control"), 50 µM Fe3+, 20 µM $H_2O_2$ and 250 µM ascorbate ("Fenton"), Fenton-reaction reagents+5 µM recombinant A1M ("$\alpha_1$-microglobulin"), or Fenton-reaction reagents+5 µM AGP ("orosomucoid"). After centrifugation, the light absorbance of the supernatant was read by scanning spectrophotometry and the absorbance at 415 nm plotted against time.

FIG. 10. Heme-induced intracellular oxidation. K562 cells were labelled with 3 µM of the oxidation-sensitive probe H2DCFDA for 30 min, washed, and resuspended in fresh medium. A: The cells were cultured with heme (5-20 µM) for 2 h and analyzed with flow cytometry. B: Cells were incubated in buffer only (Δ) or with 10 µM heme (○). The cell suspension was collected after 0, 2, 6 or 20 h and analyzed with flow cytometry. C: A1M (2, 5 or 10 µM), AGP (2, 5 or 10 µM) or ascorbate (10 µM) were added to the cells prior to the addition of 10 µM heme. The cells were incubated for 2 h and analyzed with flow cytometry. D: Cells were incubated with 10 µM heme for 30 min, washed twice with PBS and then incubated with A1M (2, 5 or 10 µM) for 2 h and analyzed with flow cytometry. E: The cells were cultured for a period of 2 h with either culture medium only, heme (10 µM), A1M (10 µM) or AGP (10 µM). The cell suspension was collected and analyzed with flow cytometry. The relative fluorescence intensity of 10000 cells (excitation 488 nm, emission 530 nm) was plotted as mean of triplicates+/−sd, 100% Defined as the mean fluorescence intensity (MFI), induced by 10 µM heme. Statistical analysis was performed in the computer program Origin (Microcal Software, Inc., Version 6), comparing groups with Student's t test. *P<0.05; P<0.01; *P<0.001.

FIG. 11 Inhibition of $H_2O_2$— and Fenton reaction-induced intracellular oxidation. A and B: K562 cells were labelled with 3 µM of the oxidation-sensitive probe $H_2DCFDA$ for 30 min, washed, and resuspended in fresh medium. The cells were cultured with $H_2O_2$ (50-250 µM) for a period of 0-20 h and the cell suspension analyzed with flow cytometry (A). Ten or twenty micromolar A1M were added to the cells prior to the addition of 50 µM $H_2O_2$. The cells were cultured for 6 h and the cell suspension analyzed with flow cytometry (B). The relative fluorescence intensity of 10000 cells (excitation 488 nm, emission 530 nm) was plotted as mean of triplicates +/−sd, 100% is defined as the mean fluorescence intensity (MFI), induced by 250 µM (A) or 50 µM (B) $H_2O_2$. Statistical analysis in FIGS. A and B was performed in the computer program Origin (Microcal Software, Inc., Version 6), comparing groups with Student's t test. *P<0.05; **P<0.01. C to F: Intracellular protein thiol-oxidation was measured by SDS-PAGE according to Baty et al (7), described in Materials and Methods. A1M, 2-10 µM, was added to cells prior to the addition of 10 µM heme and visualized by fluorimetry (C) and quantified by pixel intensity analysis (E). A1M, 2-10 µM, was added prior to the addition of a mixture containing 10 µM $(NH_4)Fe(SO_4)_2$+100 µM ascorbate+20 µM $H_2O_2$ (shown as Fe in the figure) and visualized by fluorimetry (D) and quantified by pixel intensity analysis (F). One representative experiment is shown in FIGS. C and E, and D and F, respectively.

FIG. 12. Biochemical and redox properties of A1M-heme complex. K562-cells ($0.5-1\times10^6$) were incubated with buffer or 50 µM heme for 30 min, washed and then incubated with 10 µM A1M for 2 h. After centrifugation, the supernatants were analyzed. A: Gel-filtration was performed on a 25 ml-Superose 12 HR 10/30 column using a Fast Performance Liquid Chromatography (FPLC) apparatus equipped with a 0.5 ml sample injection loop, monitoring the eluate at 280 (solid line) and 405 nm (dot line) and collecting 0.5 ml fractions. The column was equilibrated and eluted with 20 mM Tris-HCl, pH 8.5; 0.1 M NaCl; 0.02% $NaN_3$. B: ABTS-radical reduction activity was measured by mixing cell supernatants (Δ: cells+heme; ●: cells+A1M; ○: cells+heme+A1M), giving a final concentration of 3 µM A1M, with 35 µM ABTS-radical in 25 mM Na-phosphate, pH 8, reading the absorbance at 735 nm at regular intervals. Control reaction: 3 µM A1M+10 µM heme without cells (■). C: The reaction rates were calculated as the absolute values of the slopes of a line drawn by regression analysis of the points during the first 40 s, including time-point zero. Identical numbers of cells were used for the comparison of the ABTS-reduction rates. All values represent the mean and SD from three separate experiments. Statistical analysis was performed in the computer program Origin (Microcal Software, Inc., Version 6), comparing groups with Student's t test. *P<0.05.

FIG. 13. A: Inhibition of oxidant-induced HO-1-expression. Real-time PCR was used to examine the expression of the HO-1 mRNA in K562 cells exposed to heme, hydrogen peroxide or a mixture of $(NH_4)Fe(SO_4)_2$, hydrogen peroxide and ascorbate (Fenton reaction). The HO-1 expression was also analyzed with the addition of A1M to all the conditions. B-C: Inhibition of heme-induced cell death. K562 cells were cultured with heme, with or without A1M or AGP for 4 h. The cell suspension was collected, mixed with 10 µM PI (final concentration) and analyzed with flow cytometry. The percentage PI-positive cells (=dead cells) of 10000 cells (PE-channel, filtersetting 556 LP and 576/26 BP) was plotted as mean of triplicates +/−sd. D: Up-regulation of A1M. Real-time PCR was used to examine the expression of the A1M mRNA in K562 cells exposed to heme, hydrogen peroxide or a mixture of $(NH_4)Fe(SO_4)_2$, hydrogen peroxide and ascorbate (Fenton reaction). E: Silencing of A1M-expression. K562 cells were transfected with 5 nM A1M-specific siRNA, cultured for 24 h, washed, loaded with $H_2DCFDA$ as described in Materials and Methods (right panel) and exposed to 20 µM heme for 2 h. Cells were then analyzed by real time-PCR (left panel) or flow cytometry (right panel). RNA-extraction, cDNA-preparation and PCR-amplification was performed as described in Materials and Methods. The relative fluorescence intensity of 10000 cells (excitation 488 nm, emission 530 nm) was plotted as mean of triplicates +/−sd, 100% is defined as the mean fluorescence intensity (MFI), induced by A1M in cells challenged by 20 μM heme. All expression levels were normalized against G3DPH and are depicted in the figure as ΔΔCt. Statistical analysis was performed in the computer program Origin (Microcal Software, Inc., Version 6), comparing groups with Student's t test. *P<0.05; **P<0.01.

FIG. 14. Repair of oxidized collagen fibrils visualized by negative staining and transmission EM. Fibrils were formed by incubation of collagen I (0.4 mg/ml) for 24 h at 37° C. The fibrils were then incubated for 24 h at 37° C. with buffer (A) or hydroxyl-radicals generated by the Fenton-reaction: 100 μM $Fe^{3+}$, 200 μM $H_2O_2$, 1 mM ascorbate (Fenton-reaction) (B). A1M was then added (7 μM) and incubated for 24 h at 37° C. (C).

FIG. 15. Quantification of A1M in plasma and urine. Samples were from uncomplicated normal pregnancies (C), and women diagnosed with preeclampsia (PE). The A1M concentrations in plasma (top) and urine (bottom) were determined by RIA. The results from the analysis are plotted as a scatter of individual patient data and as mean+SEM. ***P<0.001, *P<0.05.

FIG. 16. A1M in placenta and its correlation with free haemoglobin. Samples were from uncomplicated normal pregnancies (C, ○) and women diagnosed with preeclampsia (PE, ●). The A1M protein concentration in placenta (A) was determined by RIA. Total RNA was extracted from homogenized cells, cDNA was prepared using reverse transcription and mRNA expression of A1M was analyzed using Real-Time PCR (B). Amplification was performed as described in the description. The mean normalized Ct values are shown for each group. To investigate the correlation between placental/plasma A1M and plasma haemoglobin, placental A1M (C) and plasma A1M (D) concentration of each patient sample was plotted against the plasma haemoglobin concentration (determined as described in materials and methods). The results from the analysis are plotted as a scatter of individual patient data and as mean±SEM. *P<0.05.

FIG. 17 A1M stimulates ECM growth. A: shows well organized collagen bundles (arrows) in a control placenta. B: shows a placenta perfused with free Hb, note the scattered collagen bundles. C: shows how A1M perfusion induces collagen production.

FIG. 19 shows the sequence listing of the sequences mentioned herein.

REFERENCES

Figure 1:
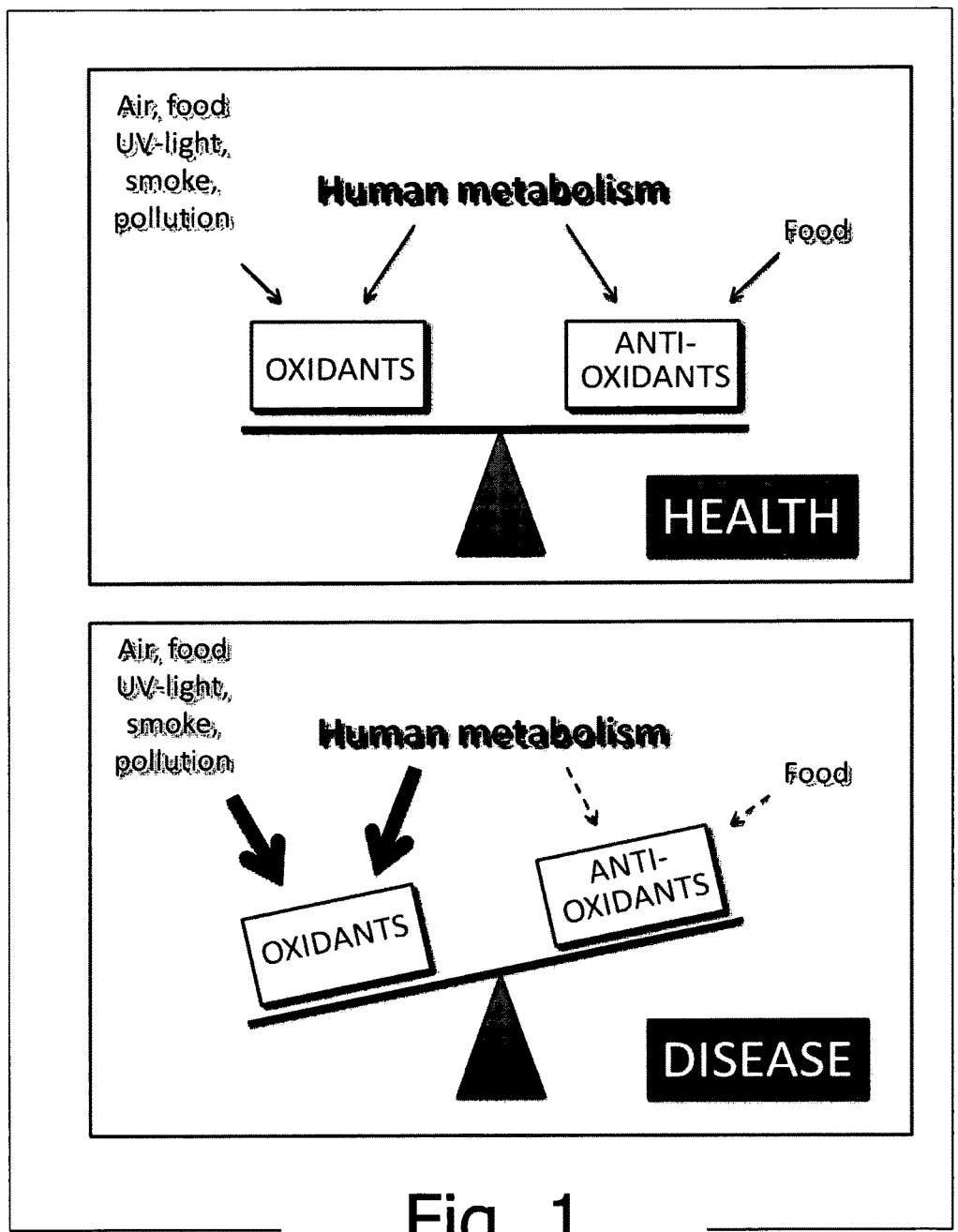
Figure 2:
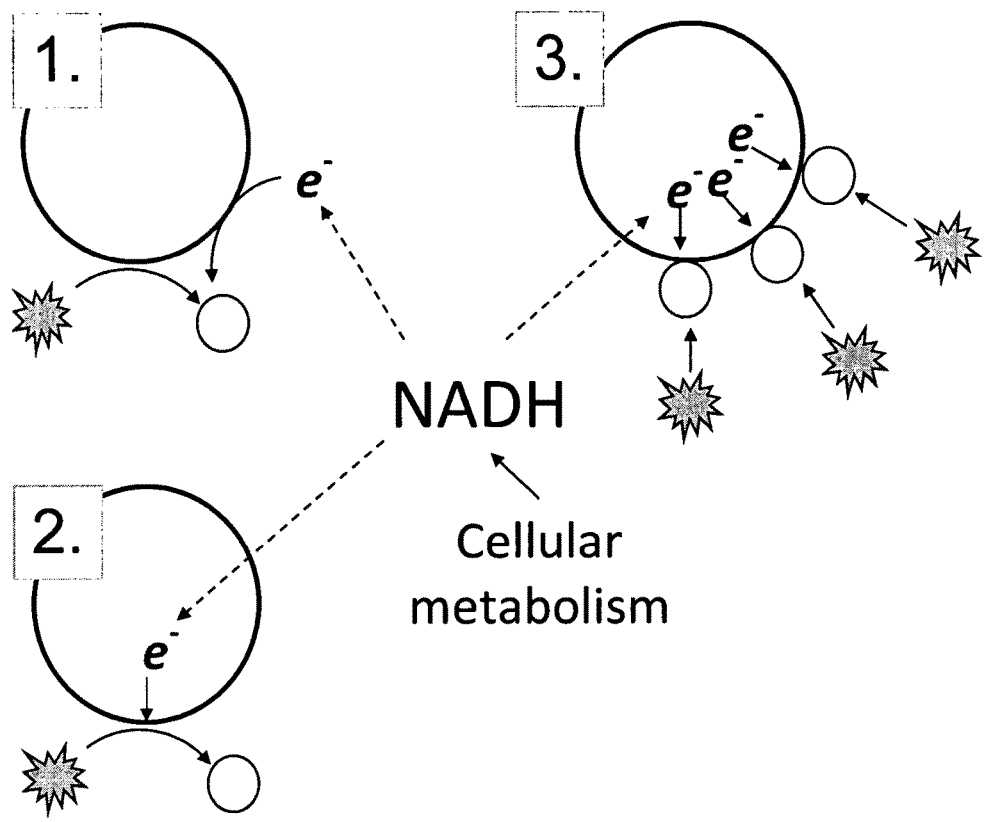
Figure 2:
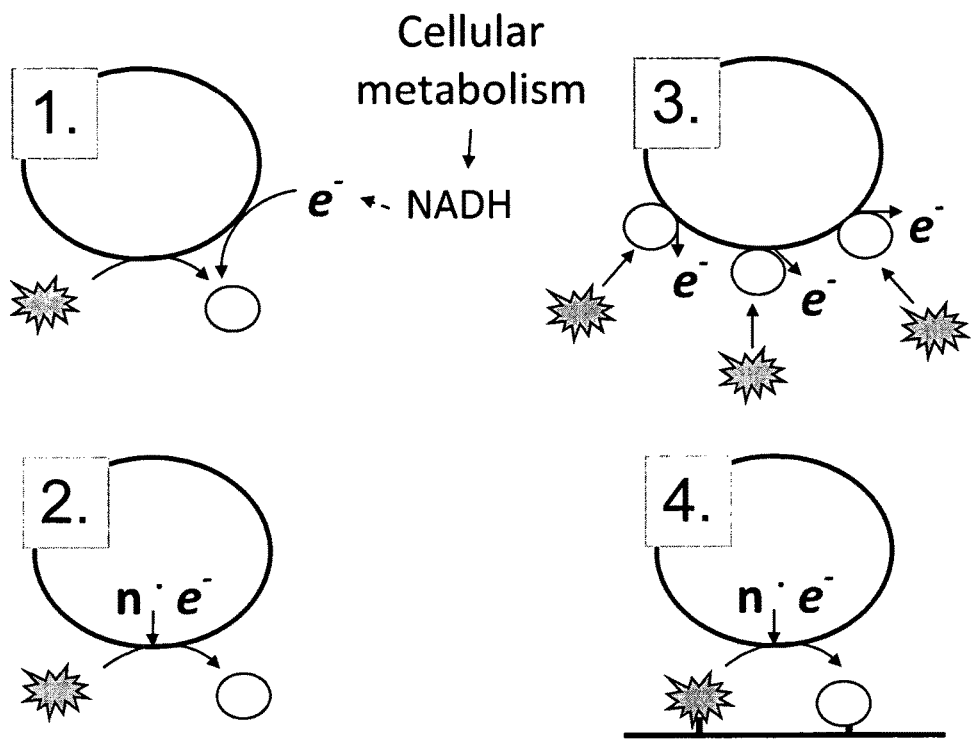
Figure 3:
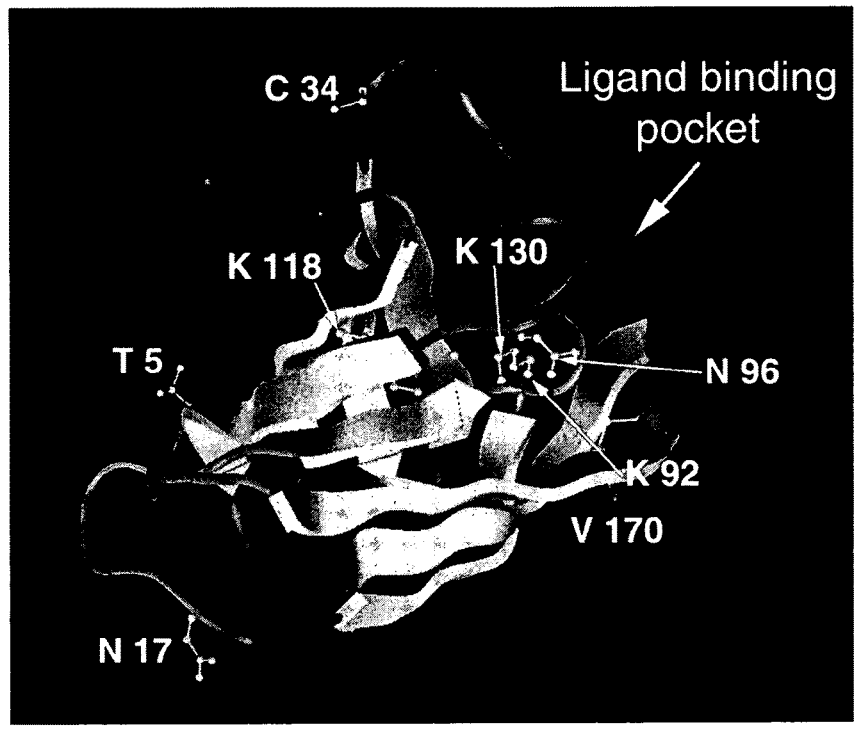
Figure 4:
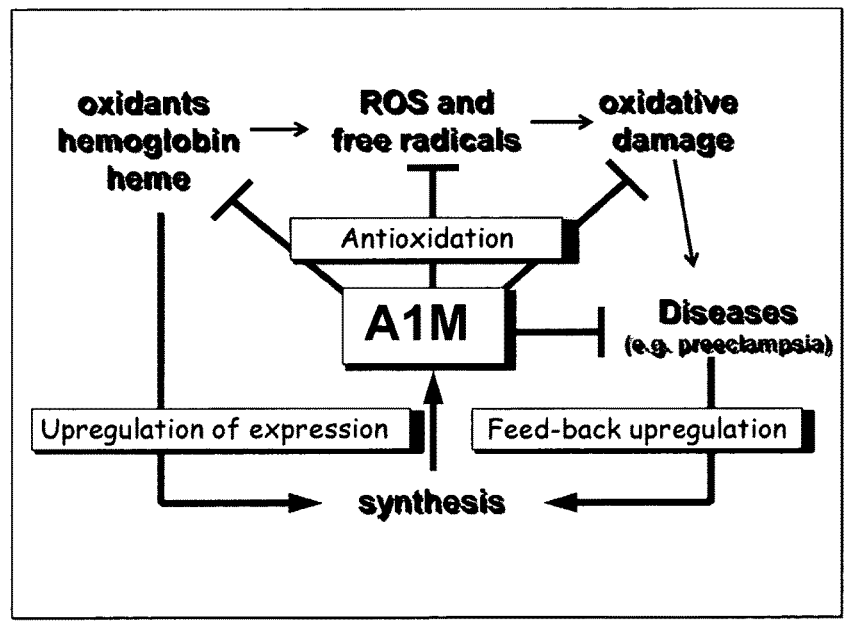
Figure 5:
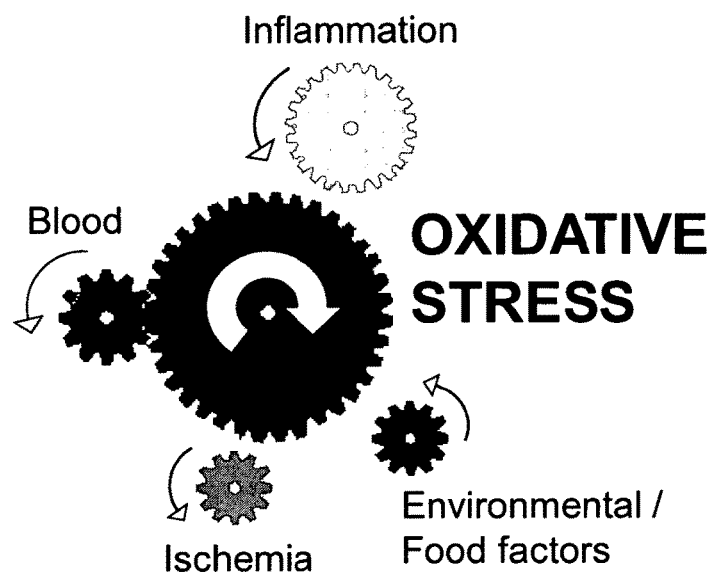
Figure 6:
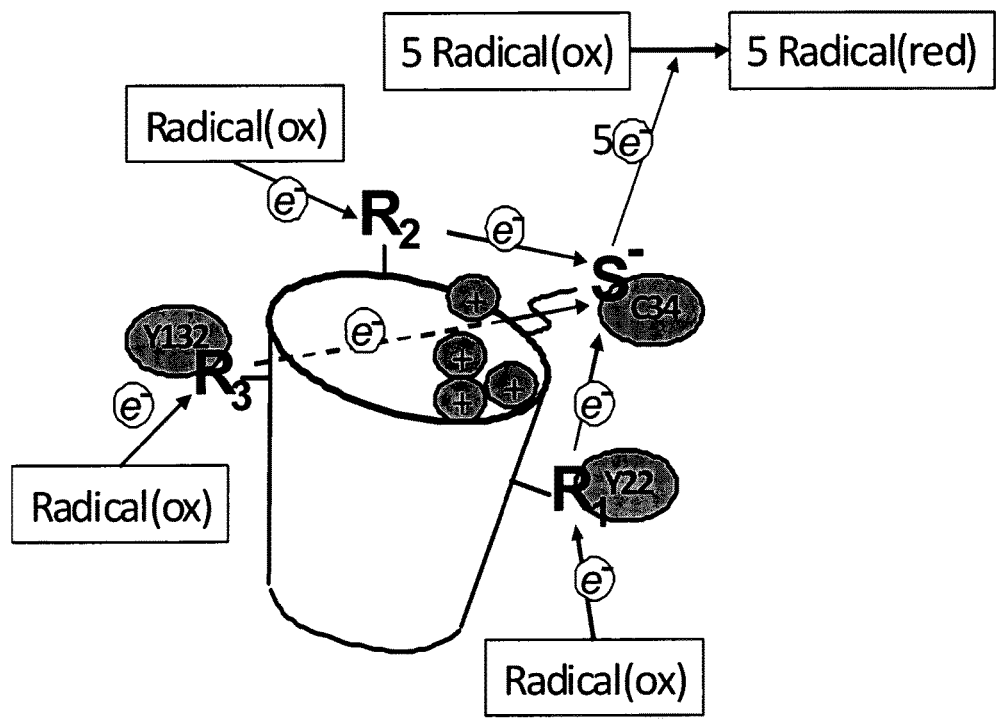
Figure 7:
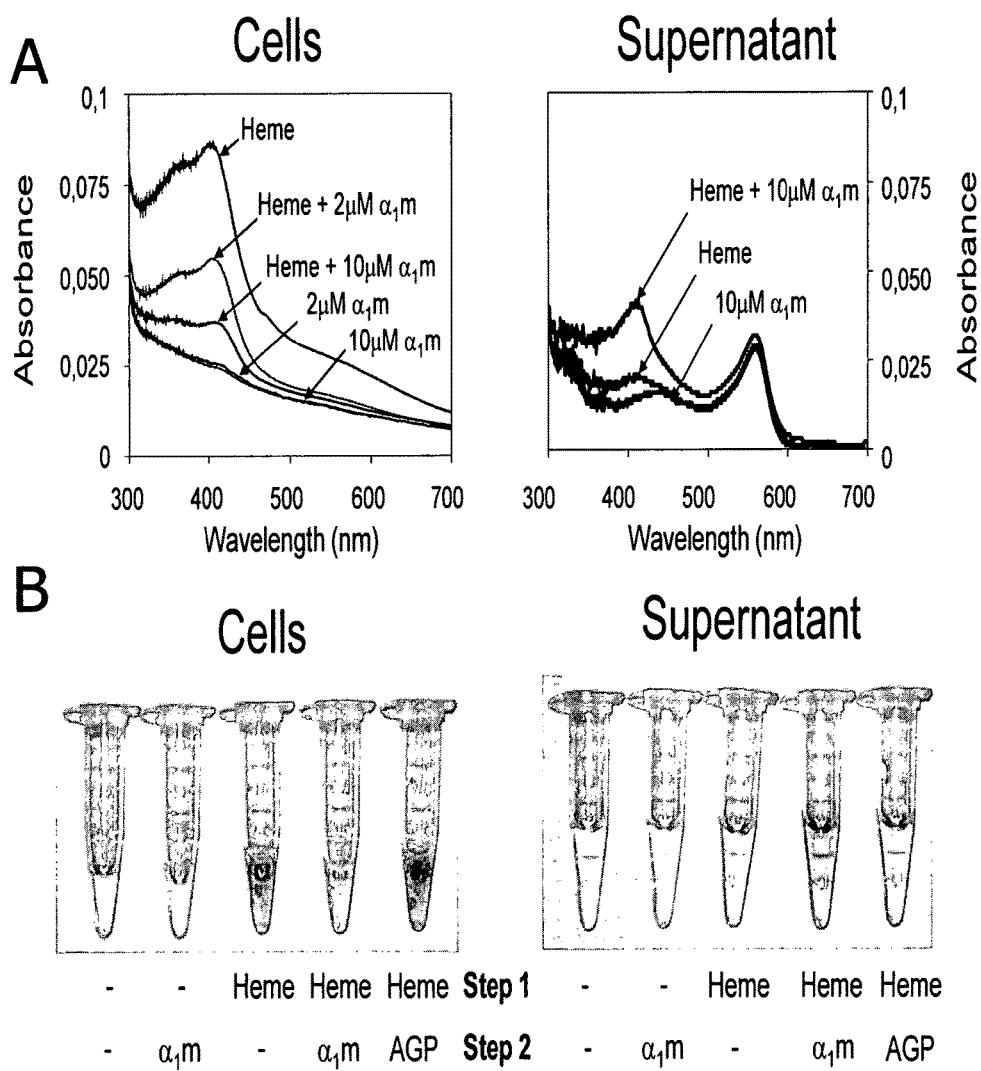
Figure 8:
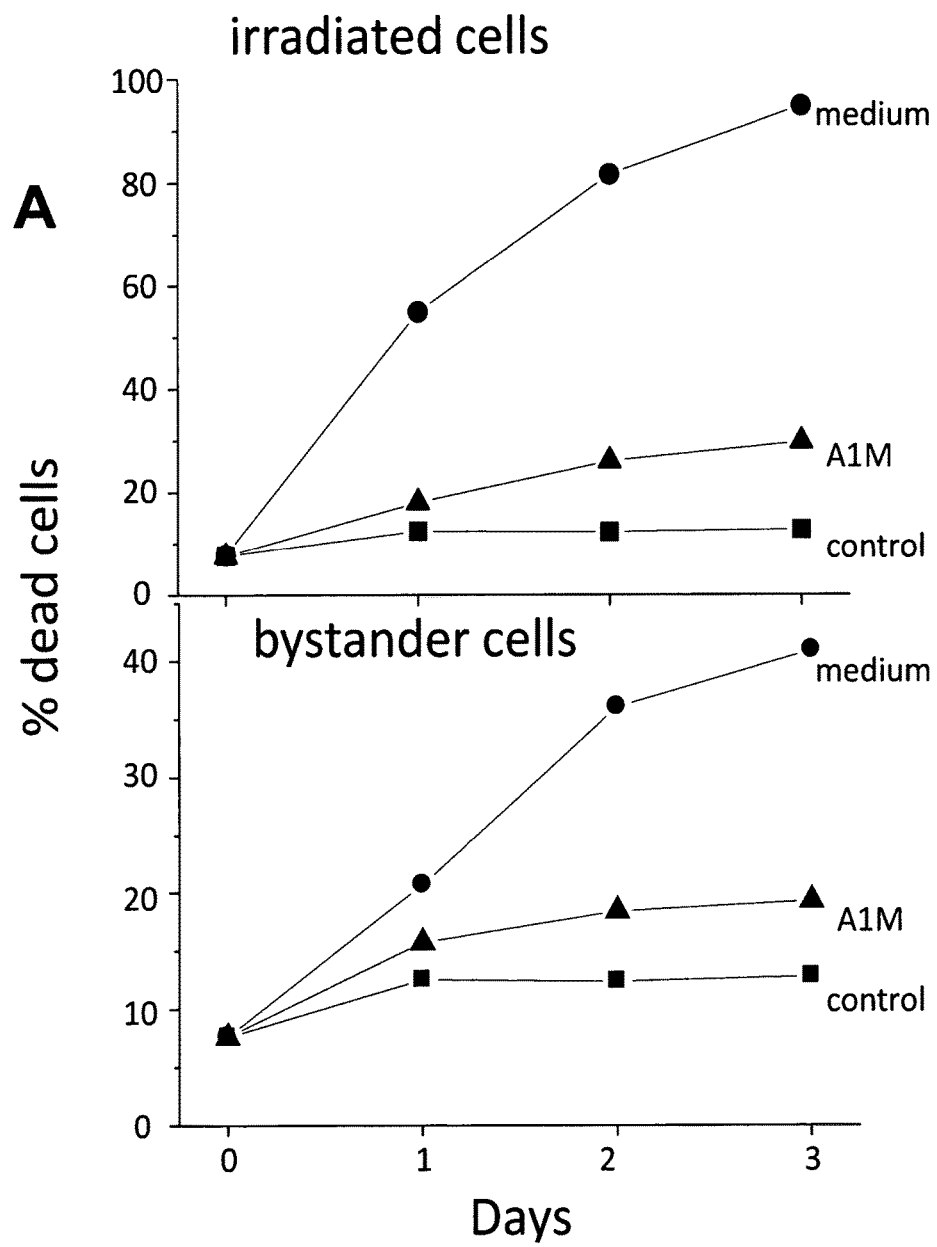
Figure 8:
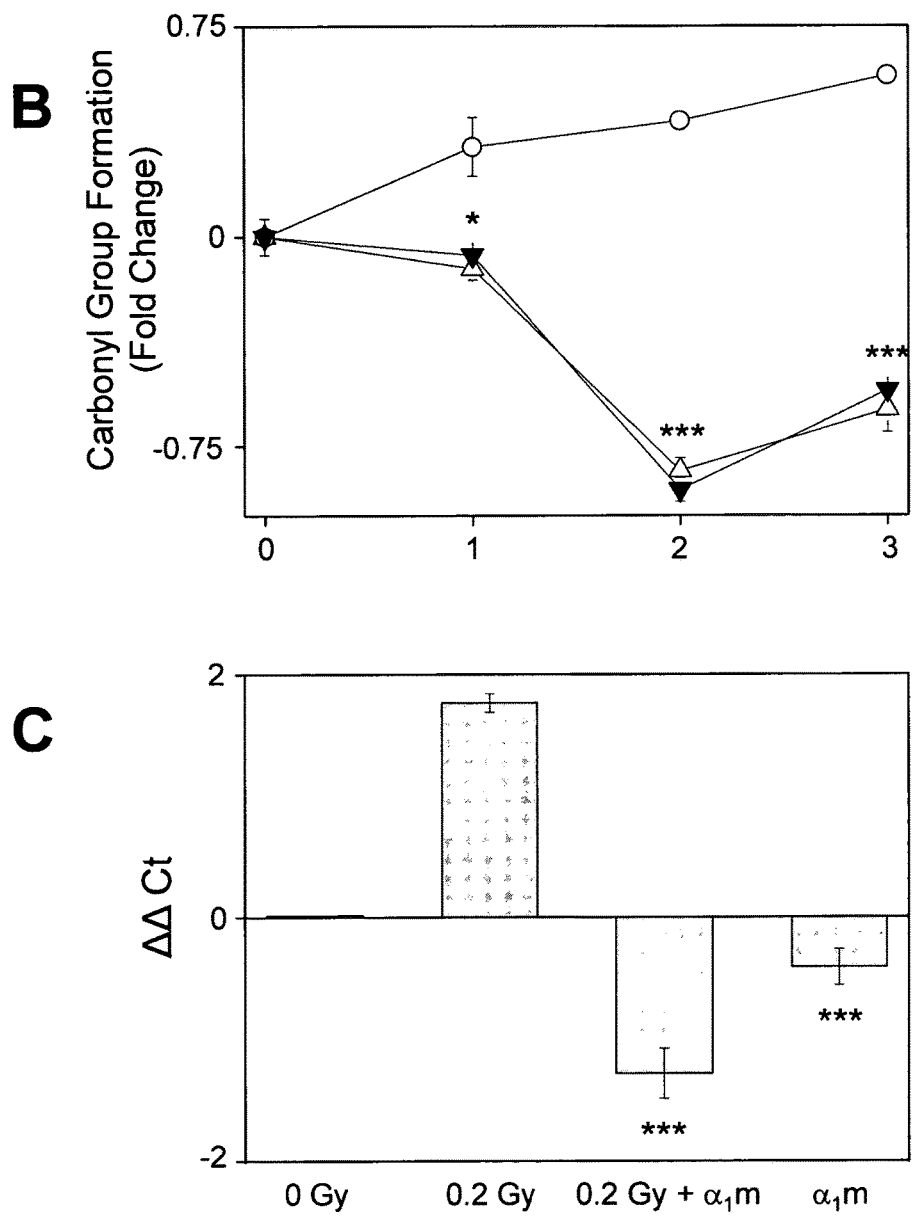
Figure 9:
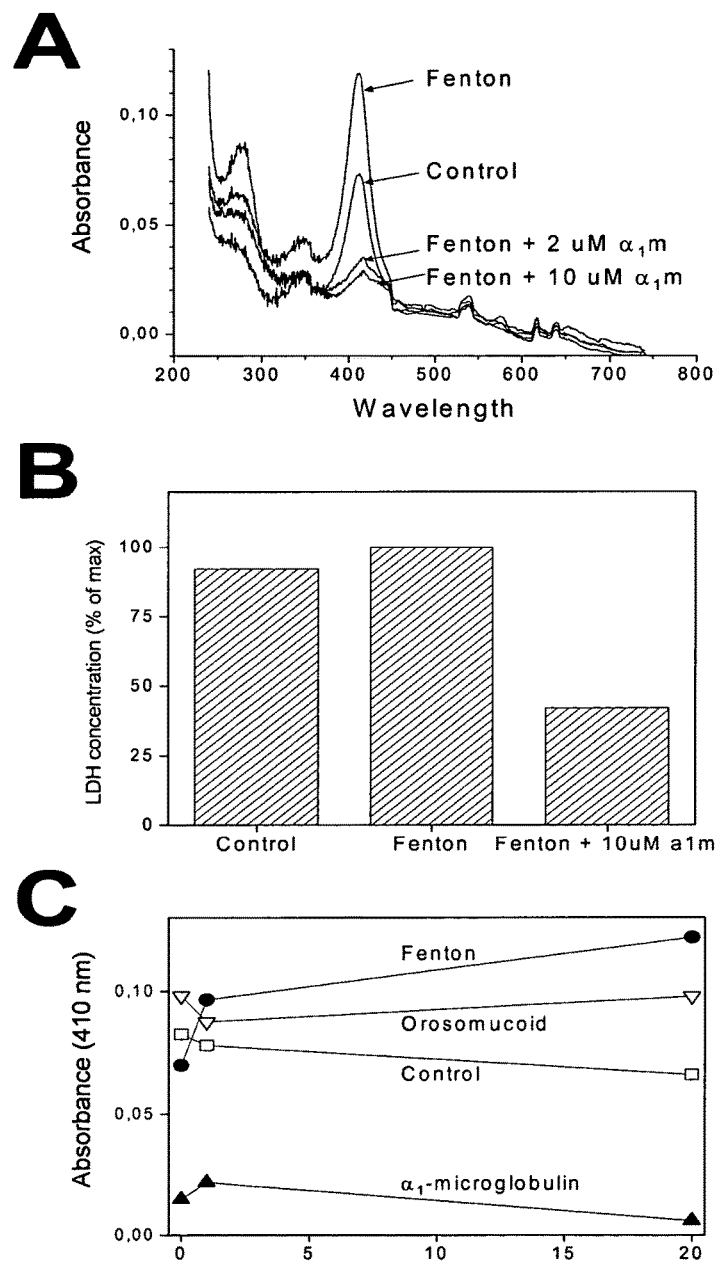
Figure 10:
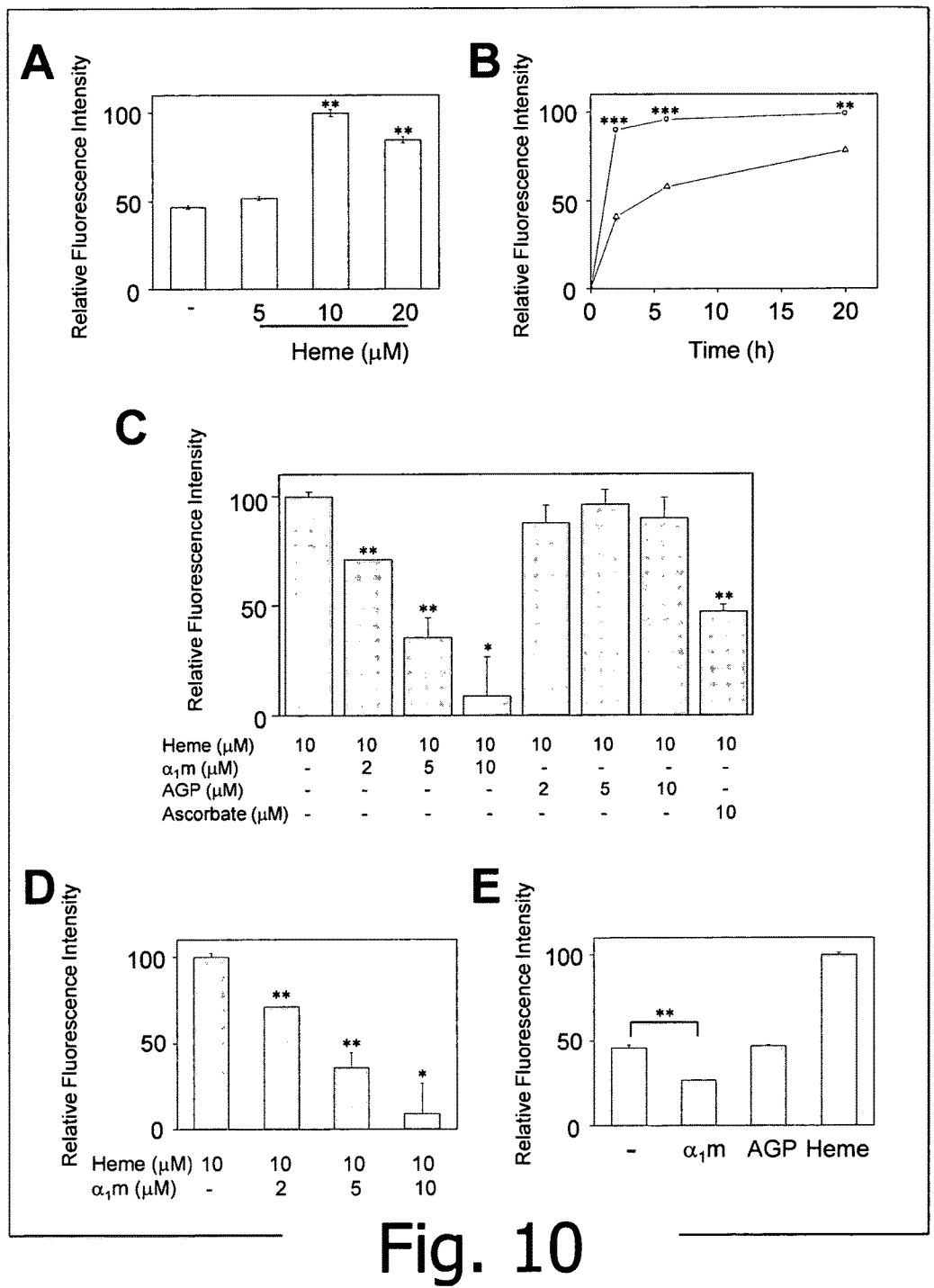
Figure 11:
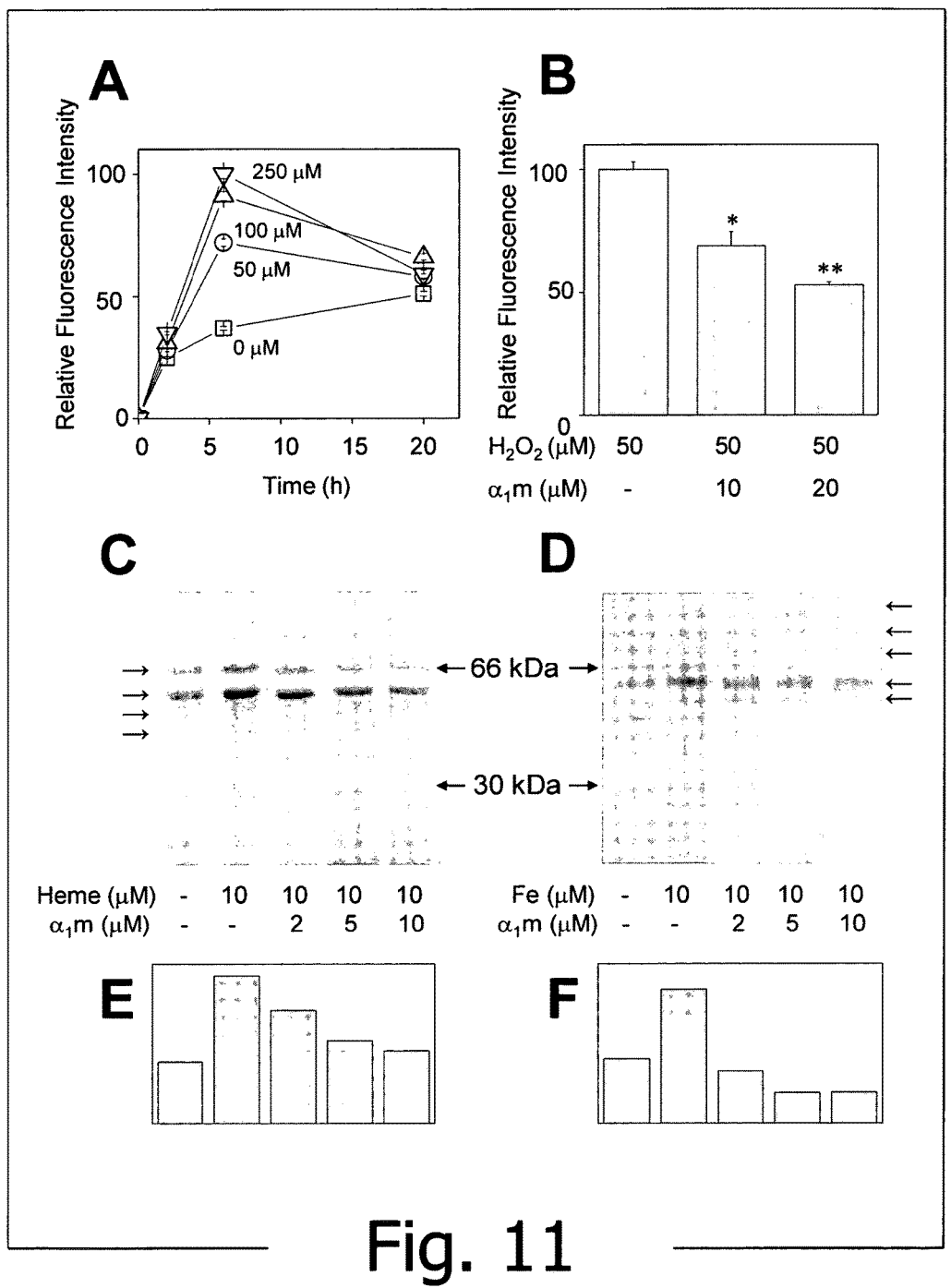
Figure 12:
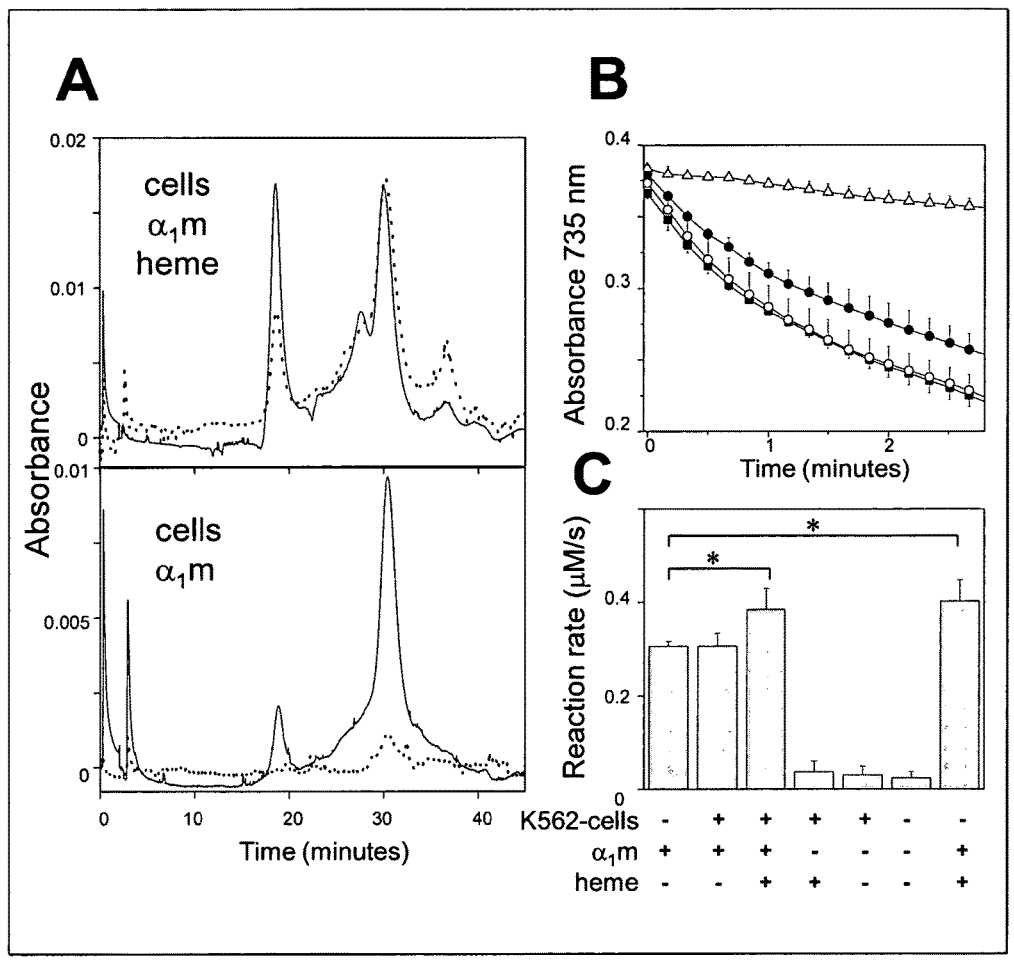
Figure 13:
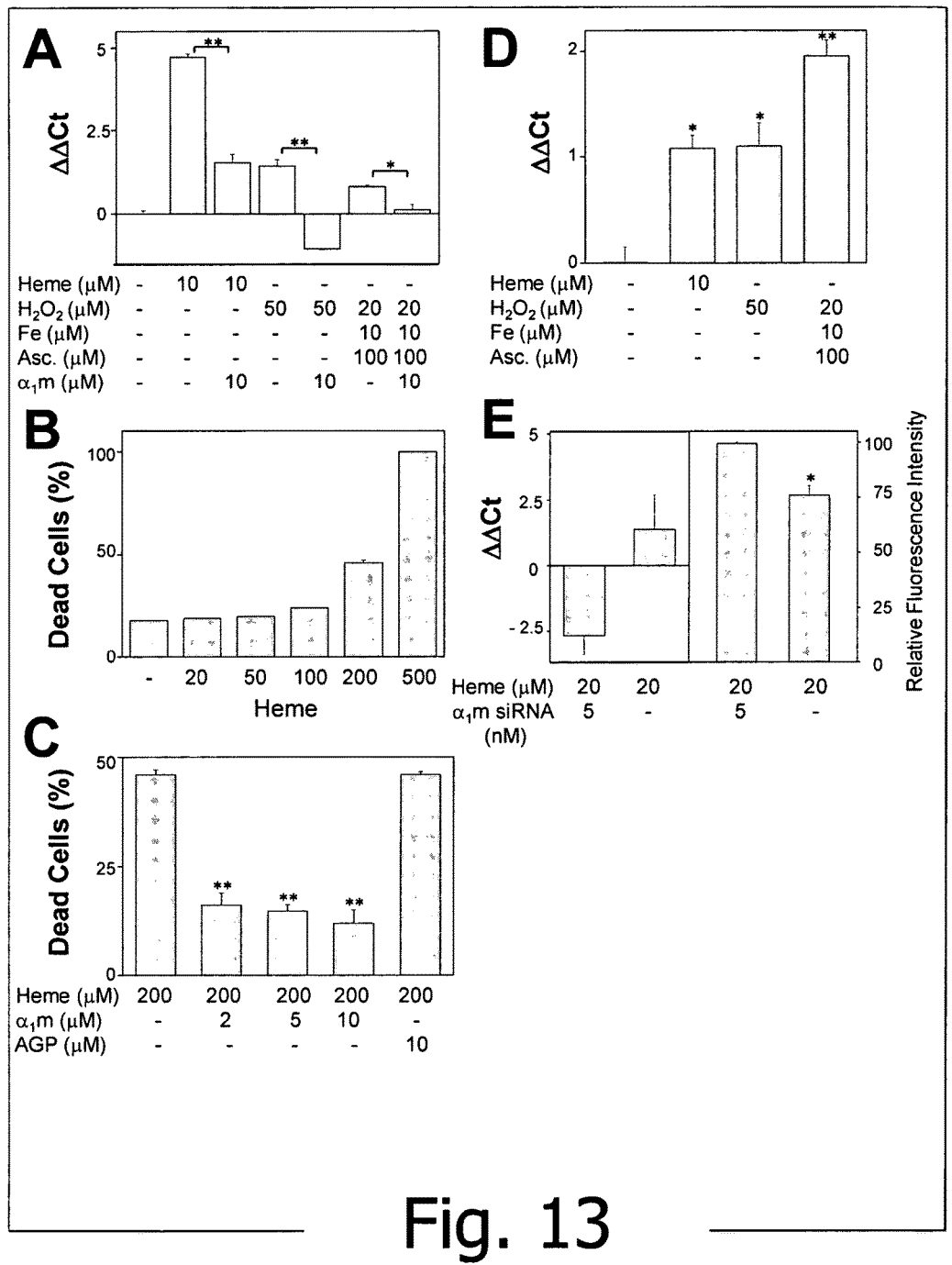
Figure 14:
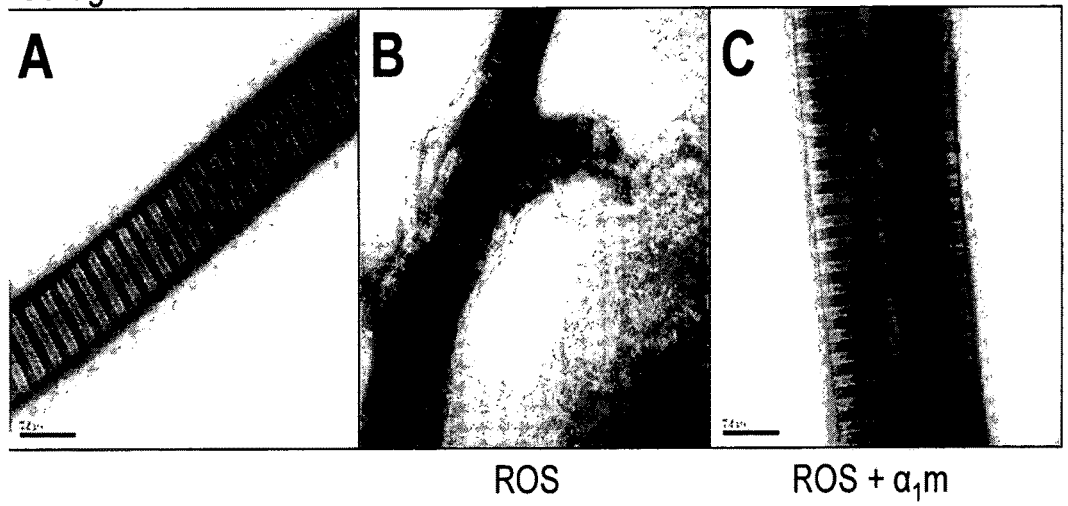
Figure 15:
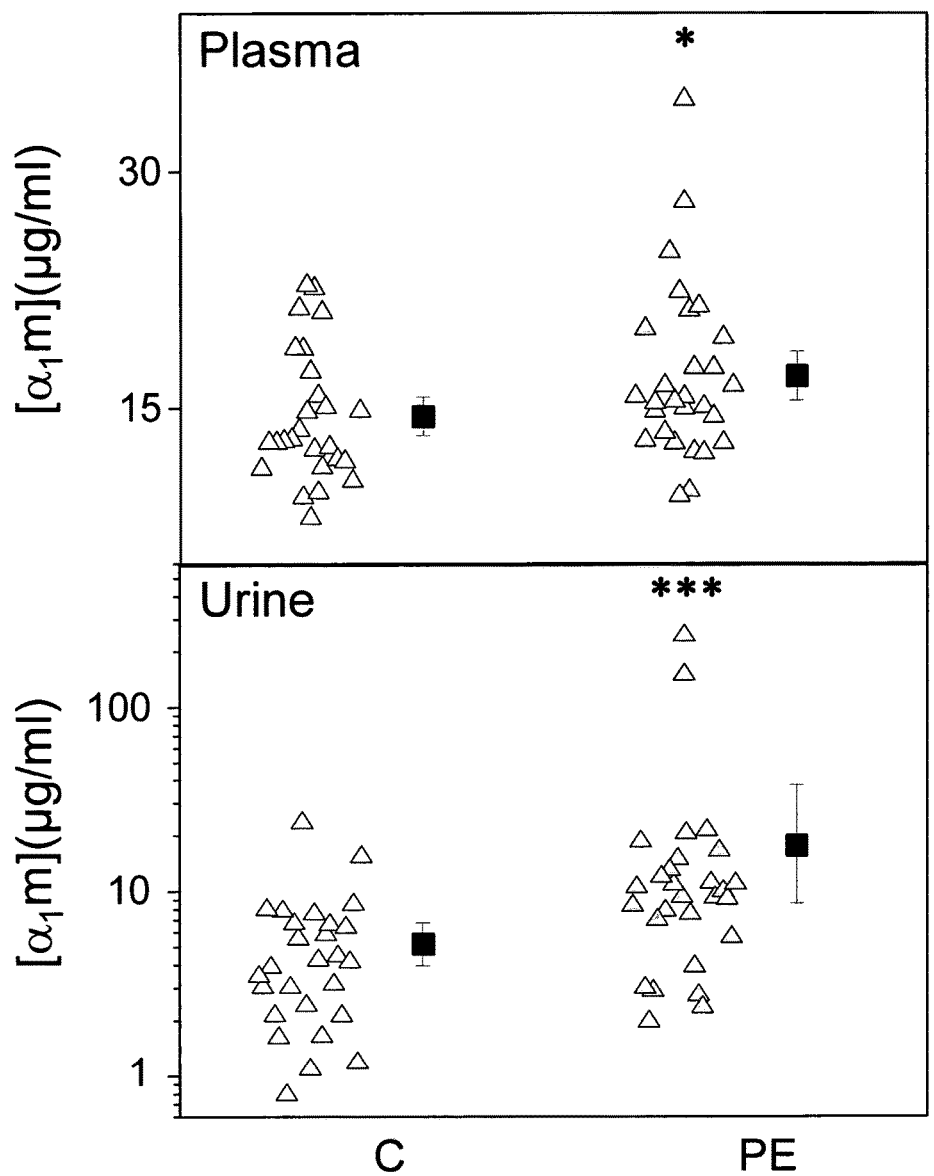
Figure 16:
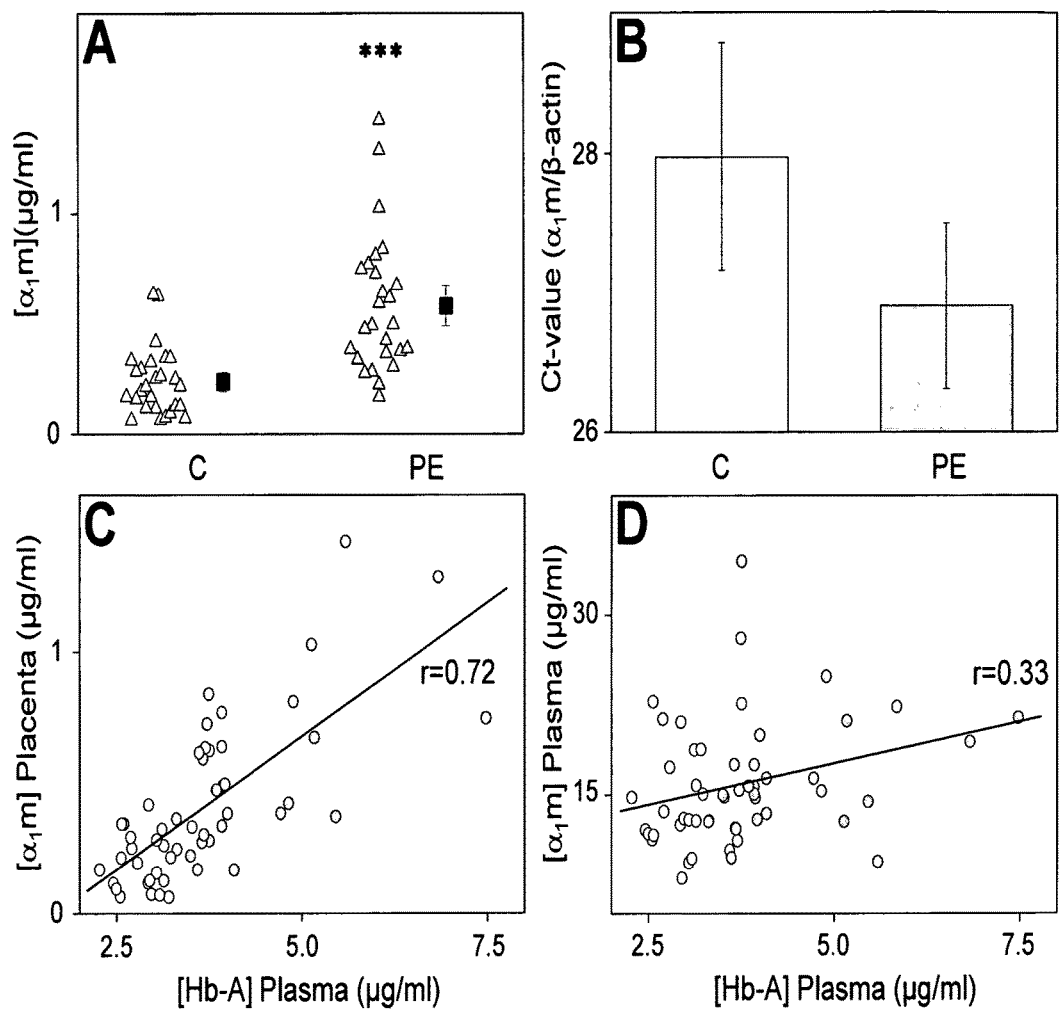
Figure 17:
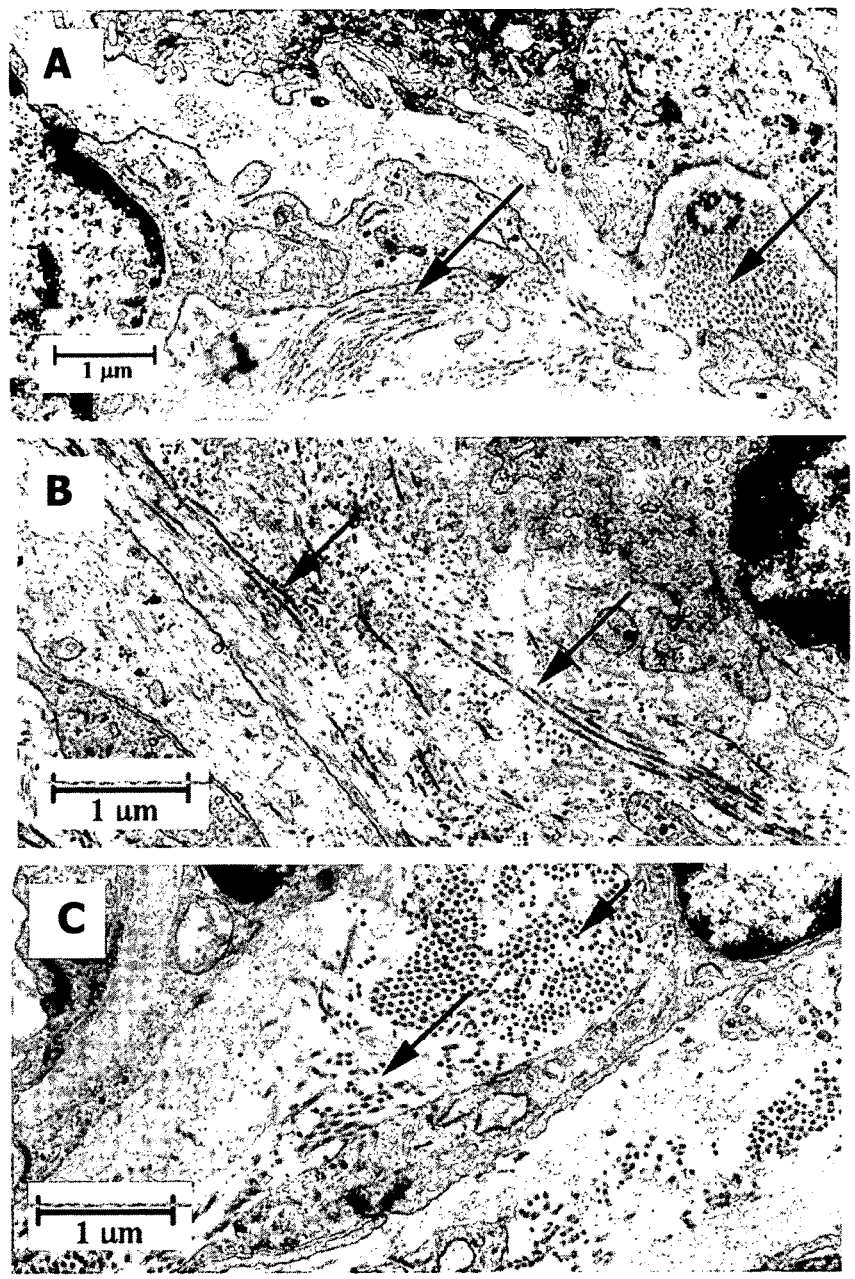
Figure 18:
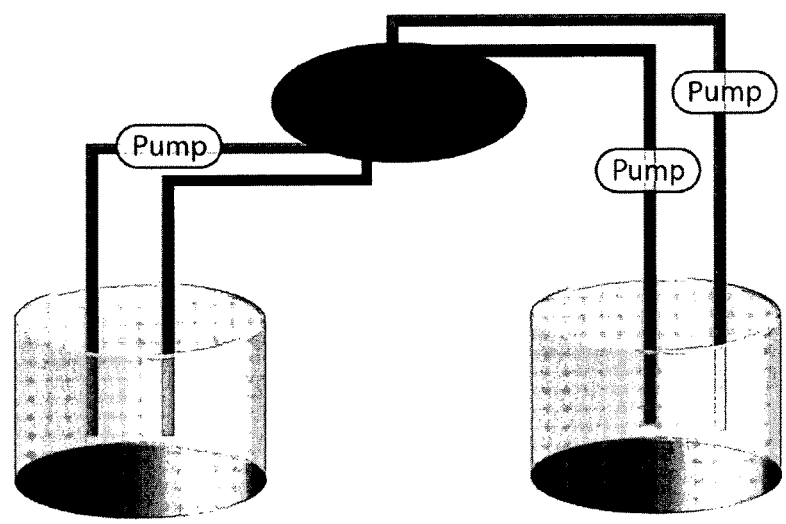
FIG. 18 illustrates the dual placenta perfusion system. The system consists of a placenta (oval) with a maternal (right) and a fetal (left) circulation.

1. Halliwell B, Gutteridge J M C (eds.) Free radicals in biology and medicine. Oxford University Press, 2002.
2. Dröge W. 2002. Free radicals in the physiological control of cell function. Physiol Rev 82, 47-95.
3. Segal A W. 2005. How neutrophils kill bacteria. Annu Rev Immunol 23, 197-223.
4. Halliwell B, Gutteridge J M. 1996. The definition and measurement of antioxidants in biological systems. Free Rad Biol Med 18, 125-126.
5. Kaumeyer J F, Polazzi J O, Kotick M P. The mRNA for a proteinase inhibitor related to the HI-30 domain of inter-α-trypsin inhibitor also encodes $α_1$-microglobulin (protein HC). Nucleic Acids Res 1986; 14(20):7839-50.
6. Sala A, Campagnoli M, Perani E, Romano A, Labò S, Monzani E, Minchiotti L, Galliano M. 2004. Human $α_1$-microglobulin is covalently bound to kynurenine-derived chromophores. J Biol Chem 279, 51033-41.
7. Allhorn M, Berggård T, Nordberg J, Olsson M L, Åkerström B. 2002. Processing of the lipocalin $α_1$-microglobulin by haemoglobin induces heme-binding and heme-degradation properties. Blood 99, 1894-1901.
8. Larsson J, Allhorn M, Åkerström B. 2004. The lipocalin $α_1$-microglobulin binds heme in different species. Arch. Biophys. Biochem. 432, 196-204.
9. Allhorn M, Klapyta A, Åkerström B. 2005. Redox properties of the lipocalin $α_1$-microglobulin: reduction of cytochrome c, haemoglobin, and free iron. Free Radic Biol Med 38, 557-67.
10. Åkerström B, Maghzal G, Winterboum C C, Kettle A J. 2007. The lipocalin $α_1$-microglobulin has radical scavenging activity. J Biol Chem 282, 31493-31503.

---

SEQUENCE LISTING

<160> NUMBER OF SEQ ID NOS: 5

<210> SEQ ID NO 1
<211> LENGTH: 183
<212> TYPE: PRT
<213> ORGANISM: Homo sapiens

<400> SEQUENCE: 1

```
Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95
```

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
            115                 120                 125

Ala Lys Leu Tyr Gly Arg Ala Pro Gln Leu Arg Glu Thr Leu Leu Gln
            130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 2
<211> LENGTH: 201
<212> TYPE: PRT
<213> ORGANISM: Homo sapiens

<400> SEQUENCE: 2

Met His His His His His His His Gly Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
            35                  40                  45

Gly Ser Thr Cys Pro Trp Leu Lys Lys Ile Met Asp Arg Met Thr Val
50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
            115                 120                 125

Tyr Ala Ile Phe Leu Thr Lys Lys Phe Ser Arg His His Gly Pro Thr
            130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
            195                 200

<210> SEQ ID NO 3
<211> LENGTH: 549
<212> TYPE: DNA
<213> ORGANISM: Homo sapiens

<400> SEQUENCE: 3
ggccctgtgc caacgccgcc cgacaacatc caagtgcagg aaaacttcaa tatctctcgg      60
atctatggga gtggtacaa cctggccatc ggttccacct gccctggct gaagaagatc      120 atggacagga tgacagtgag cacgctggtg ctgggagagg gcgctacaga ggcggagatc      180

```
agcatgacca gcactcgttg gcggaaaggt gtctgtgagg agacgtctgg agcttatgag        240
aaaacagata ctgatgggag gtttctctat cacaaatcca aatggaacat aaccatggag        300
tcctatgtgg tccacaccac ctatgatgag tatgccattt ttctgaccaa gaaattcagc        360
cgccatcatg gacccaccat tactgccaag ctctacgggc gggcgccgca gctgagggaa        420
actctcctgc aggacttcag agtggttgcc cagggtgtgg gcatccctga ggactccatc        480
ttcaccatgg ctgaccgagg tgaatgtgtc cctggggagc aggaaccaga gcccatctta        540
atcccgaga                                                                549

<210> SEQ ID NO 4
<211> LENGTH: 603
<212> TYPE: DNA
<213> ORGANISM: Homo sapiens

<400> SEQUENCE: 4
atgcatcacc atcaccatca ccatcacggt ggaggagggg gtatcgaggg ccgcggccct         60
gtgccaacgc cgcccgacaa catccaagtg caggaaaact tcaatatctc tcggatctat        120
gggaagtggt acaacctggc catcggttcc acctgcccct ggctgaagaa gatcatggac        180
aggatgacag tgagcacgct ggtgctggga gagggcgcta cagaggcgga gatcagcatg        240
accagcactc gttggcggaa aggtgtctgt gaggagacgt ctggagctta tgagaaaaca        300
gatactgatg ggaggtttct ctatcacaaa tccaaatgga acataaccat ggagtcctat        360
gtggtccaca ccacctatga tgagtatgcc atttttctga ccaagaaatt cagccgccat        420
catggaccca ccattactgc caagctctac gggcgggcgc cgcagctgag ggaaactctc        480
ctgcaggact tcagagtggt tgcccagggt gtgggcatcc ctgaggactc catcttcacc        540
atggctgacc gaggtgaatg tgtccctggg gagcaggaac cagagcccat cttaatcccg        600
aga                                                                      603

<210> SEQ ID NO 5
<211> LENGTH: 19
<212> TYPE: RNA
<213> ORGANISM: Artificial Sequence
<220> FEATURE:
<223> OTHER INFORMATION: for silencing expression of alpha-1-
      microglobulin

<400> SEQUENCE: 5
ccuauugggu ccacaccaa                                                      19
```

The invention claimed is:

1. A method of treating a subject suffering from a disease or condition involving oxidative stress and reducing oxidant levels in a subject in need thereof, the method comprising administering to the subject an amount of alpha-1-microglobulin (A1M) effective to reduce oxidant levels in the subject of from about 0.5 mg/kg to about 100 mg/kg, wherein the disease or condition involving oxidative stress is selected from the group consisting of sepsis, inflammation, arthritis, hemolytic transfusion reaction, and diabetes.

2. A method of treating a subject suffering from a disease or condition associated with the presence of free haemoglobin in a body fluid and reducing free haemoglobin levels in a subject in need thereof, the method comprising administering to the subject an amount of alpha-1-microglobulin (A1M) effective to reduce free haemoglobin levels in the subject of from about 0.5 mg/kg to about 100 mg/kg, wherein the disease or condition associated with the presence of free haemoglobin in a body fluid is selected from the group consisting of sepsis, inflammation, arthritis, hemolytic transfusion reaction, and diabetes.

3. The method according to claim 1, wherein A1M repairs or prevents oxidative damage by a combination of one or more different mechanisms.

4. The method according to claim 3, wherein said mechanisms comprise one or more of enzymatic reduction, non-enzymatic reduction and/or radical scavenging.

5. The method according to claim 1, wherein the A1M has an amino acid sequence with at least 85% identity with the amino acid sequence of human alpha-1-microglobulin set forth in SEQ ID NO: 1, including the following amino acid residues conserved from SEQ ID NO:1: Y22; C34; K69; K92; K118; K130; Y132; L180; I181; P182; and R183.

6. The method according to claim 5, wherein the A1M has an amino acid sequence with at least 90% identity with SEQ ID NO: 1.

7. The method according to claim 1, wherein the A1M is human alpha-1-microglobulin (SEQ ID NO: 1).

8. The method according to claim 1, wherein the A1M has an amino acid sequence with at least 85% identity with the amino acid sequence of human recombinant alpha-1-microglobulin set forth in SEQ ID NO: 2, including the following amino acid residues conserved from SEQ ID NO: 2: Y40; C52; K87; K110; K136; K148; Y150; L198; I199; P200; and R201.

9. The method according to claim 8, wherein the A1M has an amino acid sequence with at least 90% identity with SEQ ID NO: 2.

10. The method according to claim 1, wherein the A1M is human recombinant alpha-1- microglobulin (SEQ ID NO: 2).

11. The method according to claim 1, wherein the A1M is administered parenterally.

12. The method according to claim 1, wherein the A1M is administered locally.

13. The method according to claim 1, wherein the A1M is administered locally to a body cavity or to the skin.

14. The method according to claim 1, wherein the A1M is administered in the form of a composition comprising the A1M and a pharmaceutically acceptable excipient.

15. The method according to claim 14, wherein the pharmaceutically acceptable excipient is selected from the group consisting of solvents, pH adjusting agents, osmotically active agents, co-solvents, solubilizing agents, emulsifying agents, suspending agents, surface active agents, and wetting agents.

16. The method according to claim 2, wherein A1M repairs or prevents oxidative damage by a combination of one or more different mechanisms.

17. The method according to claim 16, wherein said mechanisms comprise one or more of enzymatic reduction, non-enzymatic reduction and/or radical scavenging.

18. The method according to claim 2, wherein the A1M has an amino acid sequence with at least 85% identity with the amino acid sequence of human alpha-1-microglobulin set forth in SEQ ID NO: 1, including the following amino acid residues conserved from SEQ ID NO:1: Y22; C34; K69; K92; K118; K130; Y132; L180; I181; P182; and R183.

19. The method according to claim 18, wherein the A1M has an amino acid sequence with at least 90% identity with SEQ ID NO: 1.

20. The method according to claim 2, wherein the A1M is human alpha-1-microglobulin (SEQ ID NO: 1).

21. The method according to claim 2, wherein the A1M has an amino acid sequence with at least 85% identity with the amino acid sequence of human recombinant alpha-1-microglobulin set forth in SEQ ID NO: 2, including the following amino acid residues conserved from SEQ ID NO: 2: Y40; C52; K87; K110; K136; K148; Y150; L198; I199; P200; and R201.

22. The method according to claim 21, wherein the A1M has an amino acid sequence with at least 90% identity with SEQ ID NO: 2.

23. The method according to claim 2, wherein the A1M is human recombinant alpha-1-microglobulin (SEQ ID NO: 2).

24. The method according to claim 2, wherein the A1M is administered parenterally.

25. The method according to claim 2, wherein the A1M is administered locally.

26. The method according to claim 2, wherein the A1M is administered locally to a body cavity or to the skin.

27. The method according to claim 2, wherein the A1M is administered in the form of a composition comprising the A1M and a pharmaceutically acceptable excipient.

28. The method according to claim 27, wherein the pharmaceutically acceptable excipient is selected from the group consisting of solvents, pH adjusting agents, osmotically active agents, co-solvents, solubilizing agents, emulsifying agents, suspending agents, surface active agents, and wetting agents.

* * * * *